(12) United States Patent
Tirosh et al.

(10) Patent No.: US 9,884,066 B2
(45) Date of Patent: Feb. 6, 2018

(54) BILE ACID-BASIC AMINO ACID CONJUGATES AND USES THEREOF

(71) Applicant: Yissum Research Development Company of the Hebrew University of Jerusalem Ltd., Jerusalem (IL)

(72) Inventors: Oren Tirosh, Ness Ziona (IL); Ira Voloshin, Ashkelon (IL); Shlomo Sasson, Jerusalem (IL); Michal Obercyger, Ramat Gan (IL); Zecharia Madar, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/895,723

(22) PCT Filed: Jun. 5, 2014

(86) PCT No.: PCT/IL2014/050505
§ 371 (c)(1),
(2) Date: Dec. 3, 2015

(87) PCT Pub. No.: WO2014/195950
PCT Pub. Date: Dec. 11, 2014

(65) Prior Publication Data
US 2016/0120880 A1 May 5, 2016

Related U.S. Application Data

(60) Provisional application No. 61/831,622, filed on Jun. 6, 2013, provisional application No. 61/921,558, filed on Dec. 30, 2013.

(51) Int. Cl.
| | | |
|---|---|---|
| *A61K 31/575* | (2006.01) | |
| *A61K 31/573* | (2006.01) | |
| *C07J 41/00* | (2006.01) | |
| *A61K 47/48* | (2006.01) | |

(52) U.S. Cl.
CPC .......... *A61K 31/575* (2013.01); *A61K 31/573* (2013.01); *A61K 47/48023* (2013.01); *A61K 47/48038* (2013.01); *C07J 41/0005* (2013.01); *C07J 41/0061* (2013.01); *C07J 41/0088* (2013.01)

(58) Field of Classification Search
CPC ................ A61K 31/573; A61K 31/575; A61K 47/48023; A61K 47/48038; C07J 41/0005; C07J 41/0061; C07J 41/0088
See application file for complete search history.

(56) References Cited

U.S. PATENT DOCUMENTS

| | | | |
|---|---|---|---|
| 5,541,348 A | 7/1996 | Ayra et al. | |
| 6,251,428 B1 | 6/2001 | Yoo | |
| 6,451,355 B1 | 9/2002 | Reisner | |
| 7,858,608 B2 | 12/2010 | Pellicciari | |
| 7,906,137 B2 | 3/2011 | Byun | |
| 2005/0260237 A1 | 11/2005 | Byun | |
| 2008/0026077 A1 | 1/2008 | Hilfinger | |

FOREIGN PATENT DOCUMENTS

| | | |
|---|---|---|
| JP | 11060594 A  *  | 3/1999 |
| WO | 2005/113008 A1 | 12/2005 |
| WO | 2009/024022 A1 | 2/2009 |
| WO | 2010/059853 A1 | 5/2010 |

OTHER PUBLICATIONS

Balakrishnan et. al., Molecular Pharmaceutics, 2006, American Chemical Society, vol. 3(3), pp. 282-292.*
Stella et. al., Prodrugs:Challenges and Rewards, Part 2, 2007, Springer, Part 3.1, pp. 5-11.*
Database CA [online] Chmical abstract service, Columbus, Ohio, US; Konishi: "Basic studies on the usefulness of ursodeoxycholic acid derivatives for clinical medicine", XP002764980, Retrieved from STN Database accession No. 2000:6859 *abstract* & Konishi, Toshio: "Basic studies on the usefulness of ursodeoxycholic acid derivatives for Clinical medicine", Yakugaku Zasshi, 120(1), 1-15 CODEN: YKKZAJ; ISSN: 0031-6903,2000.
Database Embase [Online] Elsevier science publishers, Amsterdam, NL; 1963, Peric-Golia et al: Omithocholanic acids and cholelithiasis in man, XP002764981, Database accession No. EMB-0007594416 *abstract* & science 1963, vol. 142,No. 3589, 1963, pp. 245-246, ISSN: 0036-8075.
Kim et al., (2010) Diabetes Correction in Pancreatectomized Canines by Orally Absorbable Insulin—Deoxycholate Complex. Molecular pharmaceutics, 7(3), 708-717.
Lee et al., (2005) A new drug carrier, Nα-deoxycholyl-L-lysylmethylester, for enhancing insulin absorption in the intestine. Diabetologia, 48(3), 405-411.
Lee et al., (2005) Synthesis and biological properties of insulin-deoxycholic acid chemical conjugates. Bioconjugate chemistry, 16(3), 615-620.
Zheng et al., (2010) Synthesis and in vitro evaluation of potential sustained release prodrugs via targeting ASBT. International journal of pharmaceutics, 396(1), 111-118.
Konishi et al., (1994) Chemical modification of ursodeoxycholic acid for its intravenous administration. Drug Delivery System 9(2): 125-130 abstract.
Mills et al., (1992) Biliary excretion of chenodeoxycholyl-lysylrhodamine in Wistar rats: a possible role of a bile acid as a carrier for drugs. Biochim Biophys Acta 1126(1): 35-40.

(Continued)

*Primary Examiner* — Sarah Pihonak
(74) *Attorney, Agent, or Firm* — Vorys, Sater, Seymour & Pease LLP

(57) ABSTRACT

Compositions and methods for treating diseases or disorders associated with the metabolic syndrome using conjugates of bile acids with basic amino acids or a decarboxylated amino acid such as agmatine are provided. Further provided are bile acid-basic amino acid conjugates including chenodeoxycholic acid with an amino acid selected from arginine, lysine, histidine, ornithine or a decarboxylated amino acid such as agmatine.

7 Claims, 17 Drawing Sheets

(56) References Cited

OTHER PUBLICATIONS

Balakrishnan et al., (2006) Influence of charge and steric bulk in the C-24 region on the interaction of bile acids with human apical sodium-dependent bile acid transporter. Mol Pharm 3(3): 282-292.

Folch et al., (1957) A simple method for the isolation and purification of total lipides from animal tissues. J Biol Chem 226(1): 497-509.

Huang et al., (2005) One-year intense nutritional counseling results in histological improvement in patients with non-alcoholic steatohepatitis: a pilot study. Am J Gastroenterol 100(5): 1072-1081.

Huijghebaert et al., (1986) Influence of the amino acid moiety on deconjugation of bile acid amidates by cholylglycine hydrolase or human fecal cultures. J Lipid Res 27(7): 742-752.

Myher et al., (1975) Identification of ornithine and arginine conjugates of cholic acid by mass spectrometry. Can J Biochem 53(5): 583-590.

Voloshin et al., (2014) L-arginine conjugates of bile acids—a possible treatment for non-alcoholic fatty liver disease. Lipids Health Dis 13: 69, 11 pages.

CAS Registry No. 142451-07-8; Jul. 17, 1992 (Jul. 17, 1992).
CAS Registry No. 142451-08-9; Jul. 17, 1992 (Jul. 17, 1992).
CAS Registry No. 142451-09-0; Jul. 17, 1992 (Jul. 17, 1992).
CAS Registry No. 156816-75-0; Aug. 5, 1994 (Aug. 5, 1994).
CAS Registry No. 892403-50-8; Jul. 13, 2006 (Jul. 13, 2006).

\* cited by examiner

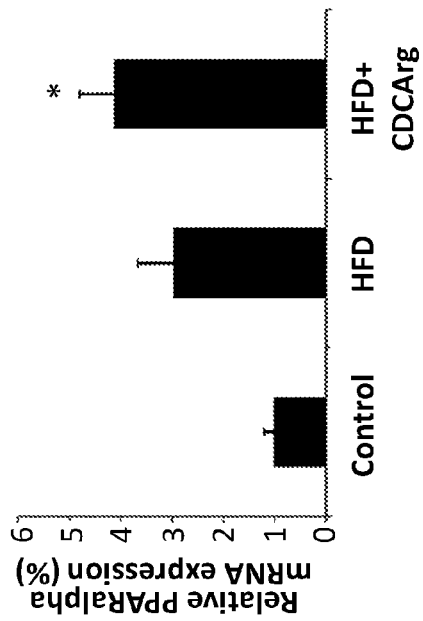
Figure 13A
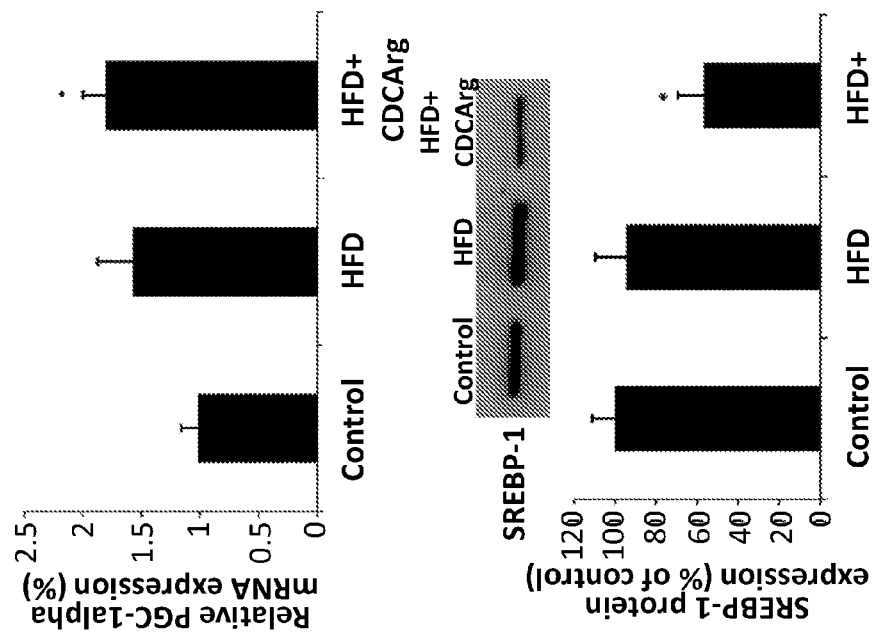
Figure 13B
Figure 13C

BILE ACID-BASIC AMINO ACID CONJUGATES AND USES THEREOF

The Sequence Listing submitted in text format (.txt) filed on Dec. 3, 2015, named "SequenceListing.txt", created on Dec. 3, 2015, 1.13 KB), is incorporated herein by reference.

FIELD OF THE INVENTION

The present invention relates to conjugates of bile acids together with basic amino acids or a decarboxylation product of a basic amino acid. The present invention further relates to the use of such conjugates in the treatment of clinical conditions associated with the metabolic syndrome, including for example obesity, dyslipidemia, diabetes and fatty liver disease.

BACKGROUND OF THE INVENTION

The metabolic syndrome (also known as syndrome X, insulin resistance syndrome), is a clustering of clinical conditions including obesity, dyslipidemia, hyperglycemia and hypertension, that greatly increases an individuals' probability for developing cardiovascular disease and other health problems, such as type-2 diabetes and stroke.

Several organizations, including for example the World Health Organization (WHO), the National Cholesterol Education Program (NCEP), the American Heart Association (AHA) and the National Heart Lung and Blood Institute (NHLBI), have attempted to formulate a definition of the metabolic syndrome, and established a set of criteria for the diagnosis of the disease. In general, the metabolic syndrome is identified by the presence of three or more of the following criteria: abdominal obesity (determined by increased waist circumference with ethnicity-specific cut-off values), elevated triglycerides or treatment for elevated triglycerides, low concentration of HDL-cholesterol or treatment for this condition, elevated blood pressure or treatment for hypertension, and impaired fasting glucose concentration or treatment with a hypoglycemic agent. The presence of just one (or two) of these conditions is not defined as a metabolic syndrome, however any of them increases the risk of developing a more serious disease.

Insulin resistance and compensatory hyperinsulinemia are known to have central etiologic roles in the development of the metabolic syndrome. Overweight and obesity have also been described as central causative components in the development of the syndrome.

Several clinical conditions are thought to be associated with the metabolic syndrome, although not part of its diagnostic criteria. One example is non-alcoholic fatty liver disease (NAFLD). Available data from clinical, experimental and epidemiological studies describe the NAFLD as the hepatic manifestation of the metabolic syndrome. It includes a spectrum of liver damage ranging from pure fatty liver, or steatosis, to nonalcoholic steatohepatitis (NASH), advanced fibrosis, and rarely, progression to cirrhosis. NAFLD is associated with the metabolic syndrome, but can also result from risk factors that do not relate to the syndrome, and may occur, for example, in non-obese and non-diabetic patients.

Several clinical conditions are thought to be complications of the metabolic syndrome, such as pre-diabetes and type-2 diabetes that is noted above.

Treatment of the metabolic syndrome typically combines lifestyle changes and medicinal treatment of the individual components of the syndrome. A combination of medicines is usually required in order to obtain satisfactory results. Common interventions include diet modification, exercise and use of a combination of pharmaceutical agents, such as cholesterol-lowering and blood pressure-lowering agents, to treat risk factors.

Bile acids are steroid acids found predominantly in the bile of mammals. In mammals, the naturally occurring bile acids are $C_{24}$ carboxylic acids which are formed from cholesterol in the liver. After their biosynthesis, their side chain may be amidated with glycine or taurine to form N-acyl conjugates which are secreted into the bile and stored in the gallbladder. During digestion, bile acids are secreted into the small intestine where they facilitate lipid absorption. The conjugated bile acids are not absorbed during digestion in the proximal small intestine because they are large, ionized molecules that are resistant to deamidation by pancreatic and mucosal carboxypeptidases. Instead, the conjugated bile acids pass to the distal ileum, where they are efficiently absorbed by an active transport system. A small fraction of the bile acids escapes absorption from the ileum and is excreted in the feces.

Synthetic conjugates of bile acids and amino acids have been described. For example, Huijghebaert et al. (1986) "Influence of the amino acid moiety on deconjugation of bile acid amidates by cholylglycine hydrolase or human fecal cultures", *Journal of Lipid Research*, 27: 742-752, report about a study of the influence of the chemical structure of the amino acid (or amino acid analogue) moiety of a number of synthetic cholyl amidates on deconjugation by cholylglycine hydrolase from *Clostridium pnfnngem*. Myher et al. (1975) "Identification of ornithine and arginine conjugates of cholic acid by mass spectrometry", *Can J Biochem*, 53:583-590, report about the preparation and mass spectrometry analysis of Nalpha-cholyl-ornithine, -arginine, and -histidine.

U.S. Pat. No. 6,251,428 discloses compositions for pharmaceutical and other uses for preparing clear aqueous solutions containing bile acids which do not form precipitates over selected ranges of pH values of the aqueous solution and methods of making such solutions.

U.S. Pat. No. 7,858,608 discloses farnesoid X receptors (FXR) modulators which can be used for the treatment of cholestatic disorders, in particular to bile acids derivatives wherein the $C_{24}$ carboxy group is transformed into an amido, carbamido or thiocarbamido group.

US 2005/0260237 discloses a delivery agent for delivering a biologically active agent to a warm-blooded animal that includes a hydrophobic moiety covalently bonded to a hydrophilic moiety. The hydrophobic moiety can include bile acids, sterols, or hydrophobic small molecules. The hydrophilic moiety can include alpha-amino acids, dipeptides or tripeptides, or hydrophilic small molecules. An illustrative delivery agent is $N^\alpha$-deoxycholyl-L-lysine-methylester. The delivery agent and the biologically active agent are mixed together to form a complex, which is then administered to the animal. These complexes are particularly useful for oral administration of biologically active agents, but other routes of administration may be used.

US 2008/0026077 discloses a method for the delivery of a therapeutic to epithelial cells through the use of a bile acid conjugated to a peptide, the peptide being ionically charged at physiological pH.

There remains a medical need for more effective compositions and methods for treating clinical conditions associated with the metabolic syndrome. There is a further need for novel molecules particularly useful for meeting said medical need.

SUMMARY OF THE INVENTION

The present invention provides compositions and methods for treating diseases or disorders associated with obesity and with the metabolic syndrome. The compositions and methods provided herein utilize conjugates of bile acids with basic amino acids, such as arginine and lysine according to some embodiments, which were found to be highly effective in improving clinical manifestations of the syndrome. In some embodiments, conjugates of bile acids with agmatine, the decarboxylation product of arginine, are used. The present invention further provides novel conjugates comprising the bile acid chenodeoxycholic acid or ursodeoxycholic acid, with at least one basic amino acid selected from arginine, lysine, histidine and ornithine, or with the decarboxylated amino acid agmatine.

The present invention is based in part on the finding that consumption of a bile acid-basic amino acid conjugate by mice fed a high fat diet (HFD) reduced, or even prevented, adverse physiological outcomes of this diet. As exemplified herein below, mice fed a HFD supplemented with the conjugate showed significantly reduced body weight gain compared to mice fed a HFD without the conjugate, despite increased food consumption. In addition, in contrast to mice who consumed the HFD only, the mice that also received the conjugate showed similar levels of total cholesterol, triglycerides and glucose in the blood as mice that consumed low fat diet only as control, without any liver damage. As further exemplified herein below, administration of the conjugate to mice fed a HFD for several weeks, after the onset of liver damage and after significant body weight gain has been observed, was shown to ameliorate liver steatosis, correct hepatomegaly, and prevent further body weight gain despite continued consumption of the HFD.

The hitherto described synthetic conjugates of bile acids with amino acids, such as basic amino acids, have been suggested mainly as delivery agents for therapeutic substances, to improve the bioavailability of the therapeutic substances. It is now disclosed for the first time that such conjugates have therapeutic benefits by themselves, and can be utilized for the treatment of the metabolic syndrome and related conditions.

According to one aspect, the present invention provides a pharmaceutical composition for use in the treatment of a disease or disorder associated with metabolic syndrome comprising as an active ingredient a compound having the structure of Formula III or a pharmaceutically acceptable salt thereof:

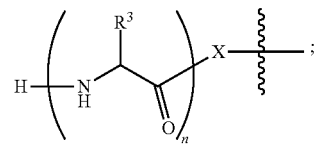

(III)

wherein:
(i) A is selected from:

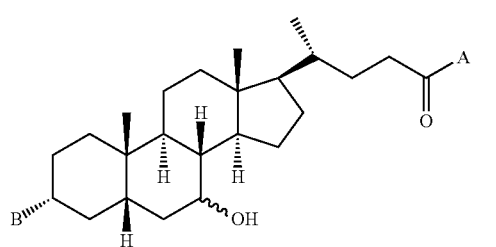

and

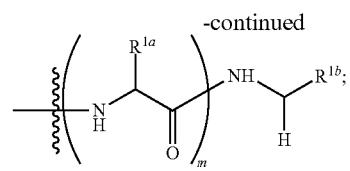

-continued

B is OH;
m is an integer of 1 to 10;
$R^{1a}$ independently at each occurrence (out of the m occurrences) represents the side chain of arginine, lysine, histidine or ornithine;
$R^{1b}$ is the side chain of agmatine; and
$R^2$ represents H, $C_1$-$C_4$ alkyl or M wherein M is a counter-ion;
or
(ii) A is —$OR^4$;
B is:

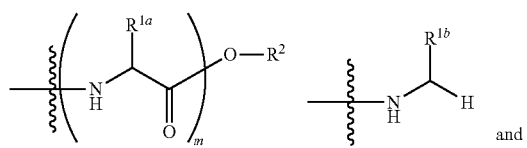

n is an integer of 1 to 10;
X is O or NH;
$R^3$ independently at each occurrence (out of the n occurrences) represents the side chain of arginine, lysine, histidine or ornithine; and
$R^4$ represents H, $C_1$-$C_4$ alkyl or M wherein M is a counter-ion.

According to another aspect, the present invention provides a method for treating a disease or disorder associated with metabolic syndrome in a subject in need thereof, the method comprising the step of administering to the subject a pharmaceutical composition comprising as an active ingredient a compound having the structure of Formula III or a pharmaceutically acceptable salt thereof.

In some embodiments, the pharmaceutical composition comprises a compound selected from the group consisting of:
(i) a compound having the structure of Formula (Ia) or a pharmaceutically acceptable salt thereof:

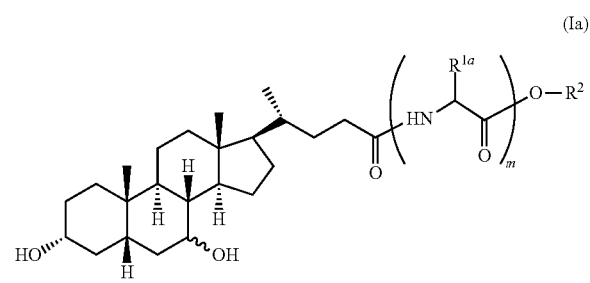

(Ia)

wherein
m is an integer of 1 to 10;
$R^{1a}$ independently at each occurrence represents the side chain of arginine, lysine, histidine or ornithine; and
$R^2$ represents H, $C_1$-$C_4$ alkyl or M wherein M is a counter-ion;

(ii) a compound having the structure of Formula (Ib) or a pharmaceutically acceptable salt thereof:

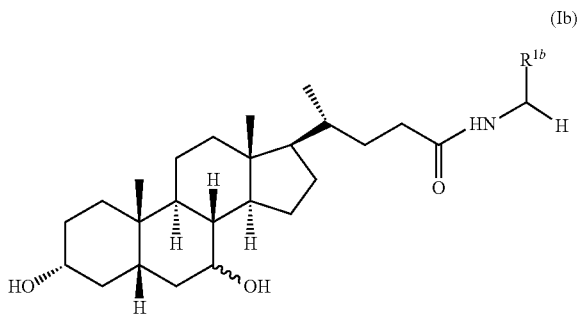

(Ib)

wherein
$R^{1b}$ is the side chain of agmatine; and
(iii) a compound having the structure of Formula (Ic) or a pharmaceutically acceptable salt thereof:

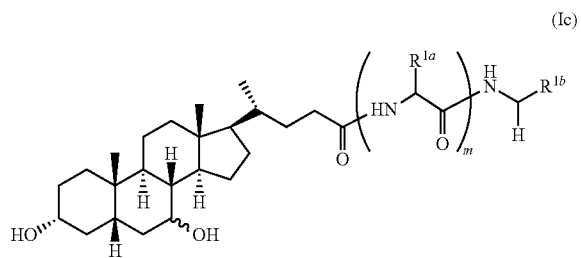

(Ic)

wherein $R^{1a}$ and $R^{1b}$ are as defined above.

In some embodiments, the pharmaceutical composition comprises a compound having the structure of Formula (II) or a pharmaceutically acceptable salt thereof:

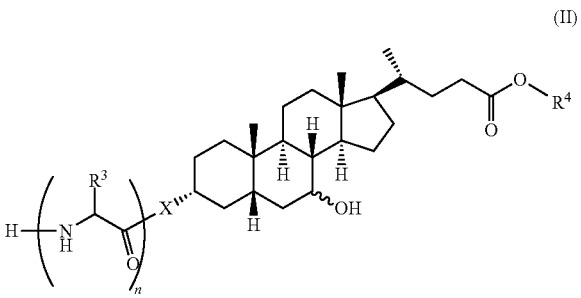

(II)

wherein
X is O or NH;
n is an integer of 1 to 10;
$R^3$ independently at each occurrence represents the side chain of arginine, lysine, histidine or ornithine; and
$R^4$ represents H, $C_1$-$C_4$ alkyl or M wherein M is a counter-ion.

It is understood that, in the compound of Formula (Ia), $(-NH-C(R^{1a})-C(=O)-)_m$ represents a lysine residue, an arginine residue, a histidine residue or an ornithine residue when m=1; or a combination thereof when m is greater than 1.

For m=1, each amino acid in the conjugate represents a separate embodiment of the present invention. For m>1, each combination of amino acids in the conjugate represents a separate embodiment of the invention.

It is further understood that, in the compound of Formula (Ib), $-NH-C(R^{1b})H$ represents an agmatine residue.

It is yet further understood that, in the compound of Formula (II), $(-NH-C(R^3)-C(=O)-)_n$ represents a lysine residue, an arginine residue, a histidine residue or an ornithine residue when n=1; or a combination thereof when n is greater than 1.

For n=1, each amino acid in the conjugate represents a separate embodiment of the present invention. For n>1, each combination of amino acids in the conjugate represents a separate embodiment of the invention.

According to the principles of the present invention, both (D)- and (L)-amino acid derivatives, as well as their racemic derivatives, are encompassed within the present invention. Thus, the groups $(-NH-C(R^{1a})-C(=O)-)_m$ or $(-NH-C(R^3)-C(=O)-)_n$ represent a D-lysine, L-lysine, D-arginine, L-arginine, D-histidine, L-histidine, D-ornithine, or L-ornithine residues, or their racemates when m or n are equal to 1, or any possible combination thereof when m or n are greater than 1. Each possibility represents a separate embodiment of the present invention.

In some embodiments, X is NH. In other embodiments, X is O. In preferred embodiments, $R^2$ and $R^4$ are each ethyl.

In some embodiments, the conjugate is a derivative of chenodeoxycholic acid (i.e., the OH moiety at C-7 is in the alpha position). In other embodiments, the conjugate is a derivative of urosodeoxycholic acid (i.e., the OH moiety at C-7 is in the beta position). Each possibility represents a separate embodiment of the present invention.

In some embodiments, $R^2$ is ammonium, an alkali metal cation or an alkaline earth metal cation. Each possibility represents a separate embodiment of the present invention.

In some embodiments, $R^4$ is ammonium, an alkali metal cation or an alkaline earth metal cation. Each possibility represents a separate embodiment of the present invention.

In some embodiments, M is selected from the group consisting of $Na^+$, $Mg^{++}$, $Ca^{++}$ and ammonium. Each possibility represents a separate embodiment of the present invention.

Several preferred compounds according to the present invention are represented by the structure of compound (1), compound (2), compound (3), compound (4), compound (5), compound (6), compound (7), compound (8), compound (9), compound (10), compound (11) and compound (12), and pharmaceutically acceptable salts thereof. The structures of these compounds are provided in the detailed description hereinbelow. Each possibility represents a separate embodiment of the present invention.

In some embodiments, the disease or disorder associated with metabolic syndrome is selected from the group consisting of obesity, excessive weight, dyslipidemia, hyperglycemia, hyperleptinemia, hyperinsulinemia pre-diabetes, type-2 diabetes, hypertension, a fatty liver disorder, including for example, NAFLD. Each possibility represents a separate embodiment of the present invention.

In some embodiments, the disease or disorder associated with the metabolic syndrome is selected from the group consisting of obesity and overweight. Each possibility represents a separate embodiment of the invention.

As used herein, the terms "obesity" and "overweight" refer to two conditions of abnormal or excessive body fat accumulation, differing in the extent of body fat accumulation. The formal definitions of obesity and overweight by the World Health Organization are based on the Body Mass Index (BMI), which is calculated as body weight in kilograms per height in meters squared (kg/m$^2$). "Overweight" is defined as a BMI greater than or equal to 25 kg/m$^2$. "Obesity" is defined as a BMI greater than or equal to 30 kg/m$^2$.

The methods and compositions of the present invention may also be used to promote weight loss and/or inhibiting weight gain in subjects with no pathology. The methods and compositions may be used to treat obesity and overweight which are not related to the metabolic syndrome, in subjects that are metabolically normal. The methods and compositions may also be used to promote weight loss and/or inhibiting weight gain in subjects who are not defined as obese or overweight, but interested in losing weight and/or maintaining a balanced body weight. Thus, in some embodiments, a method for promoting weight loss, inhibiting weight gain or both in a subject in need thereof is provided, the method comprising administering to the subject a pharmaceutical composition comprising as an active ingredient a conjugate of a bile acid with at least one basic amino acid or agmatine. In some embodiments, a pharmaceutical composition comprising such conjugate is provided, for use in promoting weight loss, inhibiting weight gain or both.

In some embodiments, the disease or disorder associated with the metabolic syndrome is dyslipidemia.

As used herein, the term "dyslipidemia" refers to an abnormal lipid profile in a subject's blood. In dyslipidemia, the concentration of one or more lipid in the blood deviates from the normal range. For example, a dyslipidemia may include one or more of the following: low high-density lipoprotein (HDL)-cholesterol, elevated total cholesterol (known as hypercholesterolemia), elevated low-density lipoprotein (LDL)-cholesterol (including any combination of LDL, intermediate-density lipoprotein (IDL), and very-low-density lipoprotein (VLDL)), elevated total cholesterol/HDL ratio, elevated triglycerides (known as hypertriglyceridemia) and elevated circulating free fatty acid levels. Each possibility represents a separate embodiment of the invention. An abnormality in the level of more than one type of lipid is sometimes referred to as a combined, or mixed, dyslipidemia.

In some embodiments, the disease or disorder associated with the metabolic syndrome is selected from the group consisting of pre-diabetes (also known as impaired glucose tolerance, and impaired fasting glucose) and type-2 diabetes (type-2 diabetes mellitus). Each possibility represents a separate embodiment of the invention.

As used herein, "pre-diabetes" and "diabetes" refer to clinical conditions characterized by abnormally high levels of blood glucose. The discrimination between pre-diabetes and diabetes is performed, inter alia, by testing fasting blood glucose, oral glucose tolerance and glycated hemoglobin (A1C) in the blood. Each test has acceptable, pre-defined ranges of values that are considered normal, indicative of pre-diabetes or indicative of diabetes. A person skilled in the art is familiar with the different criteria of each condition.

In some embodiments, the disease or disorder is hyperglycemia. As used herein, "hyperglycemia" refers to an abnormally high level of glucose in a subject's blood. In some embodiments, a method for lowering blood glucose level in a subject in need thereof is provided, the method comprising administering to the subject a pharmaceutical composition comprising as an active ingredient a conjugate of a bile acid with at least one basic amino acid or agmatine. In some embodiments, a pharmaceutical composition for use in lowering blood glucose level is provided, comprising as an active ingredient a conjugate of a bile acid with at least one basic amino acid or agmatine.

In some embodiments, the disease or disorder is hyperleptinemia. As used herein, "hyperleptinemia" refers to an abnormally high level of leptin in a subject's blood.

In some embodiments, the disease or disorder is hyperinsulinemia. As used herein, "hyperinsulinemia" refers to an abnormally high level of insulin in a subject's blood, particularly excess levels of insulin circulating in the blood than expected relative to the level of glucose (fasting glucose levels and/or glucose levels after a meal).

In some embodiments, the disease or disorder is a fatty liver disorder. In particular embodiments, the disease is a non-alcoholic fatty liver disease (NAFLD).

As used herein, "non-alcoholic fatty liver disease" refers to a condition characterized by an abnormal accumulation of fat in the liver of a subject, not due to excessive alcohol use. It includes a spectrum of liver damage ranging from a simple steatosis, in which there is an increase of fat accumulation in hepatocytes, to steatohepatitis (non-alcoholic steatohepatitis, or NASH), in which fat accumulation is accompanied by hepatocyte injury and death, as well as hepatic infiltration by inflammatory cells. NASH-related liver damage often triggers liver fibrosis. In severe cases, NASH may progress to cirrhosis and possibly hepatocellular carcinoma.

In some embodiments, the NAFLD is selected from the group consisting of steatosis and nonalcoholic steatohepatitis (NASH). Each possibility represents a separate embodiment of the invention.

In some embodiments, the disease or disorder is hypertension.

As used herein, the term "hypertension" refers to an abnormally elevated blood pressure.

According to another aspect, the present invention provides a pharmaceutical composition consisting of a conjugate of a bile acid with at least one basic amino acid or with agmatine as the sole active ingredient in a pharmaceutically acceptable carrier.

In some embodiments, the pharmaceutical composition is for use in the treatment of a disease or disorder associated with metabolic syndrome.

According to another aspect, the present invention provides a pharmaceutical composition comprising a conjugate of a bile acid with at last one basic amino acid or with agmatine as an active ingredient, and a pharmaceutically acceptable carrier, for use in the treatment of a disease or disorder associated with metabolic syndrome.

According to yet another aspect, the present invention provides a method for treating a disease or disorder associated with metabolic syndrome in a subject in need thereof, the method comprising the step of administering to the subject a pharmaceutical composition comprising a conjugate of a bile acid with at last one basic amino acid or with agmatine as an active ingredient, and a pharmaceutically acceptable carrier.

In some embodiments, a conjugate of a bile acid with a basic amino acid further comprises agmatine linked to the basic amino acid.

In additional embodiments, the conjugate is a conjugate of a bile acid with a chain of basic amino acids (for example, 2 basic amino acids, 2-5, 2-10 basic amino acids). In some embodiments, such conjugate further comprises agmatine linked to the basic amino acid located at end of the amino acid chain, at the C-terminus of the chain. Each possibility represents a separate embodiment of the present invention.

In some embodiments, the bile acid is selected from the group consisting of chenodeoxycholic acid, lithocholic acid, cholic acid, deoxycholic acid, ursodeoxycholic acid, ursocholic acid, hyocholic acid, hyodeoxycholic acid, murocholic acid, dehydrocholic acid, 7-ketodeoxycholic acid, diketocholanic acid, triketocholanic acid, isolithocholic acid, ketolithocholic acid, dehydrolithocholic acid, allocholanic acid, or a salt or ester thereof.

In some embodiments, the basic amino acid is selected from arginine, lysine, histidine and ornithine or a salt or ester thereof.

In some embodiments, the bile acid is selected from the group consisting of chenodeoxycholic acid or ursodeoxycholic acid.

In some embodiments, the basic amino acid is arginine.

In some embodiments, the conjugate comprises more than one basic amino acid.

Each possibility of bile acid and basic amino acid represents a separate embodiment of the present invention.

In some embodiments, the conjugate further comprises a linker between the bile acid and the amino acid, or between the bile acid and agmatine. In some additional embodiments, the conjugate comprises a chain of basic amino acids linked to the bile acid and a linker is presented between the bile acid and the first amino acid of the chain, located at the N-terminus of the chain. Each possibility represents a separate embodiment of the present invention.

In some embodiments, the conjugate is a compound of Formula (Ia) as described above. In additional embodiments, the conjugate is a compound of Formula (Ib) as described above. In yet additional embodiments, the conjugate is a compound of Formula (Ic) as described above. In other embodiments, the conjugate is a compound of Formula (II) as described above.

In some embodiments, the conjugate is selected from the group consisting of compound (1), compound (2), compound (3), compound (4), compound (5), compound (6), and compound (7) and pharmaceutically acceptable salts thereof.

Typically, the methods of the present invention comprise systemic administration of the pharmaceutical composition. In some embodiments, administering is performed by a route of administration selected from the group consisting of oral, rectal, intravenous, intramuscular, intradermal, subcutaneous and intranasal. Each possibility represents a separate embodiment of the invention. In particular embodiments, administering is performed by oral administration.

Typically, the pharmaceutical compositions of the present invention are formulated for systemic administration. In some embodiments, the pharmaceutical compositions are formulated for a route of administration selected from the group consisting of oral, rectal, intravenous, intramuscular, intradermal, subcutaneous and intranasal. In particular embodiments, the pharmaceutical compositions are formulated for oral administration.

According to a further aspect, the present invention provides a compound selected from the group consisting of:
(i) a compound having the structure of Formula (Ia) or a pharmaceutically acceptable salt thereof:

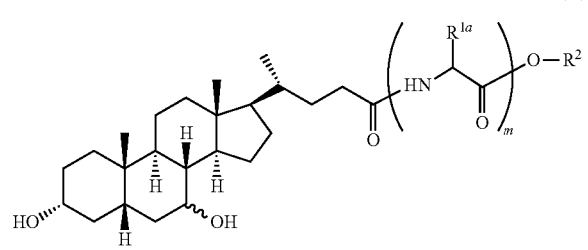

(Ia)

wherein
m is an integer of 1 to 2;
$R^{1a}$ independently at each occurrence represents the side chain of arginine, lysine, histidine or ornithine; and
$R^2$ represents H, $C_1$-$C_4$ alkyl or M wherein M is a counter-ion;
(ii) a compound having the structure of Formula (Ib) or a pharmaceutically acceptable salt thereof:

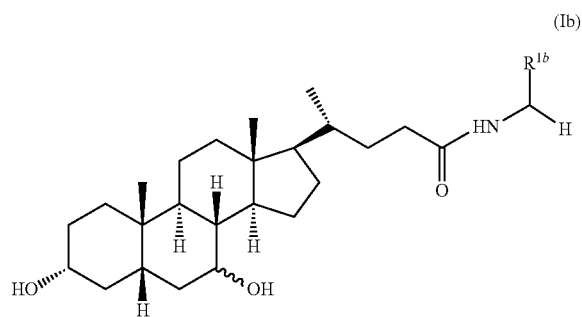

(Ib)

wherein
$R^{1b}$ is the side chain of agmatine;
(iii) a compound having the structure of Formula (Ic) or a pharmaceutically acceptable salt thereof:

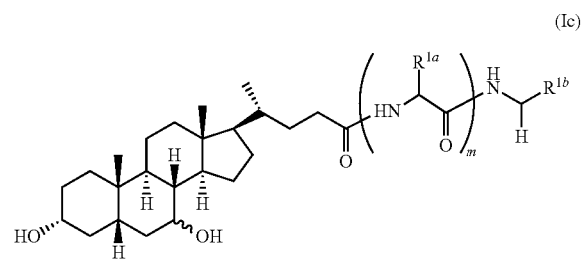

(Ic)

wherein $R^{1a}$ and $R^{1b}$ are as defined above; and
(iv) a compound having the structure of Formula (II) or a pharmaceutically acceptable salt thereof:

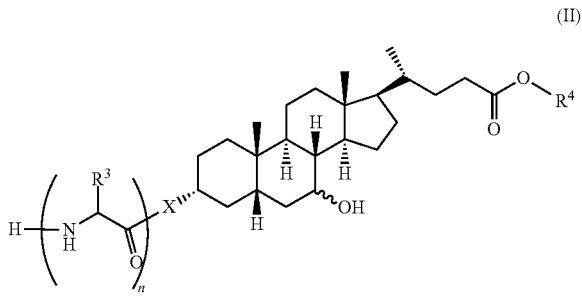

(II)

wherein
X is O or NH;
n is an integer of 1 to 2;
$R^3$ independently at each occurrence (out of the n occurrences) represents the side chain of arginine, lysine, histidine or ornithine; and
$R^4$ represents H, a $C_1$-$C_4$ alkyl or M wherein M is a counter-ion.

In some embodiments, X is NH. In other embodiments, X is O. In some embodiments, $R^2$ and $R^4$ are each ethyl.

In some embodiments, the compound is a derivative of chenodeoxycholic acid. In other embodiments, the compound is a derivative of urosodeoxycholic acid.

In some embodiments, $R^2$ is ammonium, an alkali metal cation or an alkaline earth metal cation. In some embodiments, M is selected from the group consisting of $Na^+$, $Mg^{++}$, $Ca^{++}$ and ammonium.

In some embodiments, the compound is selected from the group consisting of compound (1), compound (2), compound (3), compound (4), compound (5), compound (6), and compound (7) and pharmaceutically acceptable salts thereof.

In some particular embodiments, the compound has the structure of compound (1).

These and further aspects and features of the present invention will become apparent from the detailed description, examples and claims which follow.

BRIEF DESCRIPTION OF THE FIGURES

FIG. 13. Effect of CDCArg on lipogenic gene expression and energy expenditure related genes in the liver. Treatments: mice were fed with LFD for 14 weeks or with HFD for 10 weeks. At week 10 the HFD group was divided randomly into two equal groups that were pair fed. One group received HFD, while the other group received HFD+CDCArg. mRNA levels of (A) PGC1α, (B) PPARα. (C) Protein level of sterol regulatory element binding protein 1c (SREBP1). *p<0.05, statistically different from control by student t-test. GAPDH was used as housekeeping normalizing gene.

DETAILED DESCRIPTION OF THE INVENTION

Figure 1:
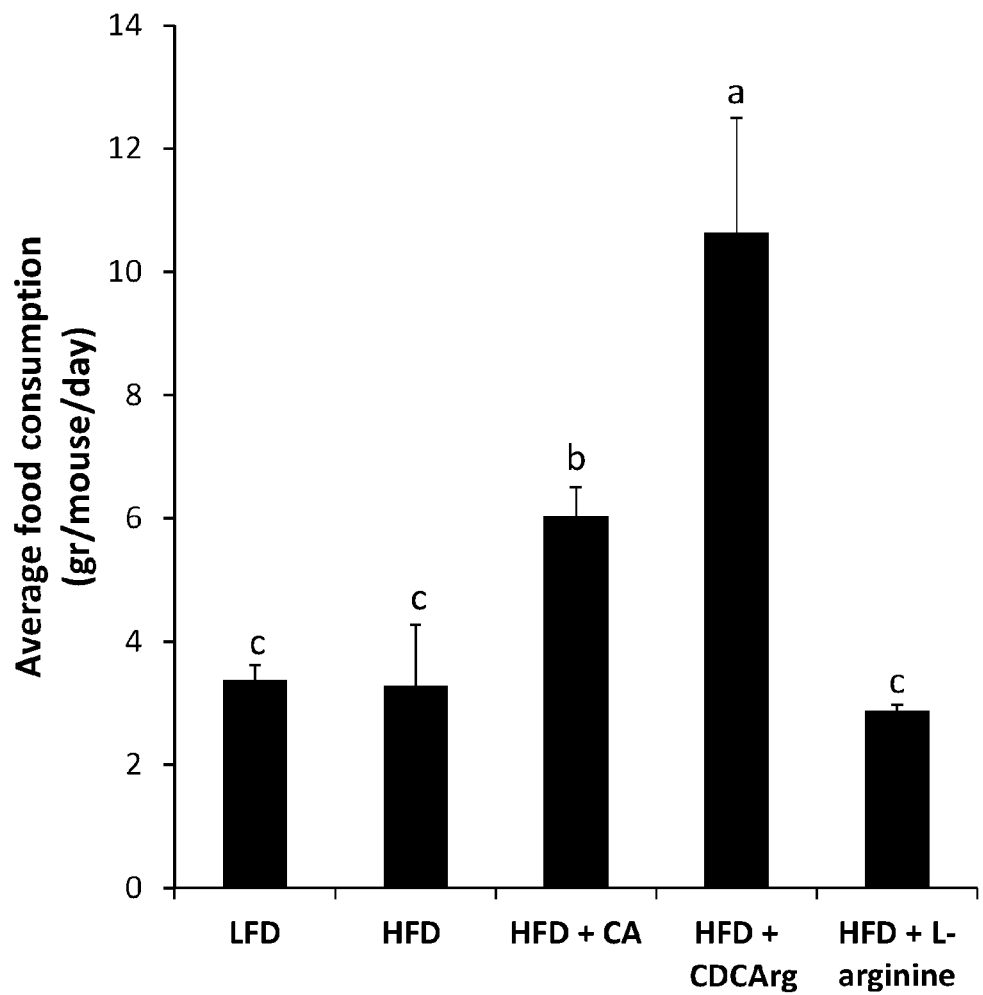
FIG. 1. Average food consumption during a five-week experiment, of mice fed a high fat diet (HFD) plus chenodeoxycholyl-arginine-ethyl ester (CDCArg) versus mice fed a control low fat diet (LFD), high fat diet with no other supplements (HFD), high fat diet plus cholic acid (HFD+CA) and high fat diet plus L-arginine in the drinking water (HFD+Arg). Results represent average daily consumption of food of weeks 2, 3, 4 and 5. Means with different letters are statistically different, P<0.05 (one way ANOVA, Post Hoc LSD test).

The present invention is directed to, inter alia, the use of bile acids conjugated to basic amino acids in the treatment of the metabolic syndrome and related conditions. The present invention is further directed to novel bile acid-basic amino acid conjugates. In some embodiments, conjugates of bile acids with agmatine, the decarboxylation product of the basic amino acid arginine, are provided. Such conjugates may be utilized by the therapeutic methods described herein.

As exemplified herein below, a conjugate of a bile acid with a basic amino acid according to embodiments of the present invention had a positive effect in reducing high fat diet (HFD)-induced obesity in mice, preventing HFD-induced fatty liver in mice, and improving metabolic status of mice fed a HFD. The conjugate was found to be safe and non-toxic to the animals in general, and to the liver in particular. This is in contrast to free bile acids, which are considered toxic to mammalian cells at high concentrations.

Chemical Definitions

The term "$C_1$-$C_4$-alkyl" used herein alone or as part of another group refers to any saturated aliphatic hydrocarbon, including straight-chain, and branched-chain. Examples of C1-4-alkyl groups include methyl, ethyl, n-propyl, isopropyl, n-butyl, sec-butyl, isobutyl and t-butyl.

The term "$C_1$-$C_6$ alkylene" denotes a bivalent radical of 1 to 6 carbon atoms (e.g., —CH$_2$—, —CH$_2$—CH$_2$— and the like).

The term "$C_2$-$C_6$ alkenylene" denotes a bivalent radical of 2 to 6 carbon atoms containing at least one carbon-carbon double bond (e.g., —CH═CH— and the like).

The term "bile acid residue" means the moiety which remains after the bile acid has been conjugated to the amino acid (directly or through a linker). For example, when the conjugation is made through the carboxyl moiety of the bile acid R—C(═O)—OH, the residue will be R—C(═O)—. If the link is made through a hydroxyl (OH) or amino (NH$_2$) moiety, the bile acid residue will be RO— or R—NH—, depending on the type of bond being formed.

The term "amino acid residue" means the moiety which remains after the amino acid has been conjugated to the bile acid and/or to an additional amino acid and/or to agmatine. The link between the amino acid and the bile acid and/or another amino acid can be through the alpha-amino, carboxyl or side chain of the amino acid. For example, when the link is made through the alpha amino moiety, the residue will be —NH—C(R)—C(═O)OR' wherein R is the amino acid side chain and R' is H or an alkyl. Alternatively, when the link is made through the carboxy moiety, the residue will be H$_2$N—C(R)—C(═O)— where R is the amino acid side chain. When the amino acid is conjugated both through the carboxyl and the amino moieties (e.g., to a bile acid on one side and to a second amino acid or agmatine on the other), the residue can be represented as —NH—C(R)—C(═O)—. Each possibility represents a separate embodiment of the present invention. It is understood that conjugation of the amino acid to agmatine is through the carboxyl moiety of the amino acid (to an amine group of agmatine).

The term "agmatine residue" means the moiety which remains after agmatine has been conjugated to the bile acid or to a basic amino acid. The link between agmatine and the bile acid or amino acid is through an amine group of the agmatine.

For each of the conjugates exemplified herein, it is explicitly understood that both (D)- and (L)-amino acids are encompassed, as well as their racemic derivatives.

Conjugates

The conjugates of the present invention comprise bile acids conjugated to basic amino acids or to decarboxylation products thereof. In some embodiments, conjugates comprising chenodeoxycholic acid or ursodeoxycholic acid with an amino acid selected from the group consisting of arginine, lysine, histidine and ornithine are provided. Each possibility represents a separate embodiment of the invention. In some particular embodiments, the amino acid is arginine. According to other embodiments, conjugates comprising chenodeoxycholic acid or ursodeoxycholic acid with agmatine, the decarboxylation product of arginine, are provided.

In some embodiments, a conjugate of the present invention has the structure of Formula III, or a pharmaceutically acceptable salt thereof:

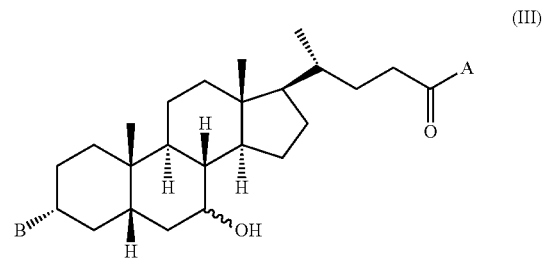

(III)

wherein either:

(i) A is selected from:

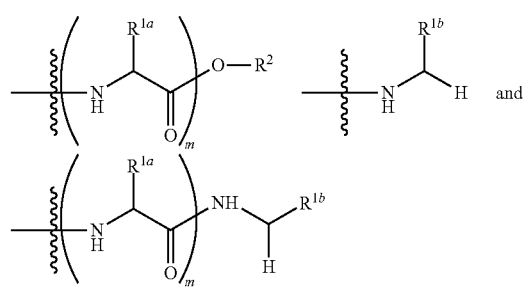

and B is OH;

m is an integer of 1 to 10;

$R^{1a}$ independently at each occurrence represents the side chain of arginine, lysine, histidine or ornithine:

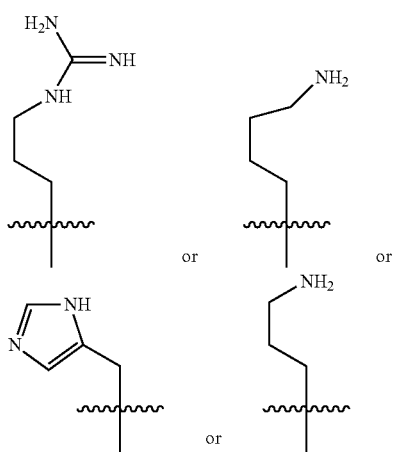

or

R<sup>1b</sup> is the side chain of agmatine:

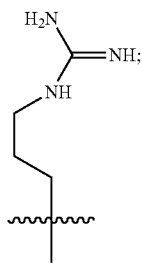 [SMILES: *CCCNC(=N)N]

and

R² represents H, C₁-C₄ alkyl or M wherein M is a counter-ion;

or (ii)

A is —OR⁴ and B is

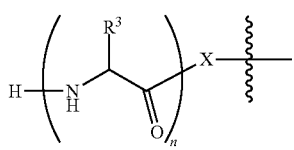

n is an integer of 1 to 10;
X is O or NH;
R³ independently at each occurrence represents the side chain of arginine, lysine, histidine or ornithine:

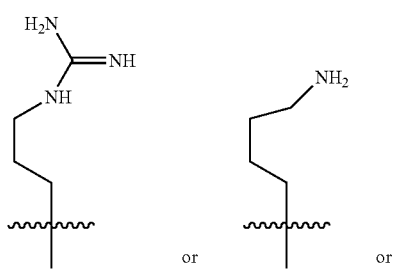

or

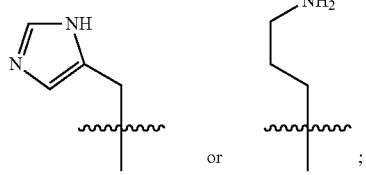

and

R⁴ represents H, a C₁-C₄ alkyl or M wherein M is a counter-ion.

In some embodiments, A is:

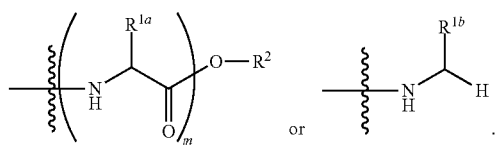

In some embodiments, the conjugate has the structure of Formula (Ia) or a pharmaceutically acceptable salt thereof:

(Ia)

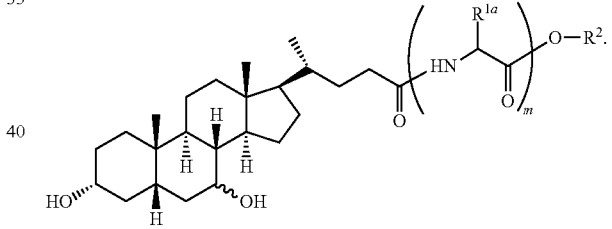

In some embodiments, the conjugate has the structure of Formula (Ib) or a pharmaceutically acceptable salt thereof:

(Ib)

In some embodiments, the conjugate has the structure of Formula (Ic) or a pharmaceutically acceptable salt thereof:

(Ic)

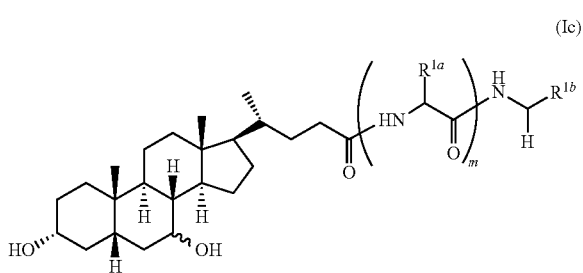

wherein:

$R^{1a}$ independently at each occurrence represents the side chain of arginine, lysine, histidine or ornithine; and $R^{1b}$ is the side chain of agmatine.

In additional embodiments, the conjugate has the structure of Formula (II) or a pharmaceutically acceptable salt thereof:

(II)

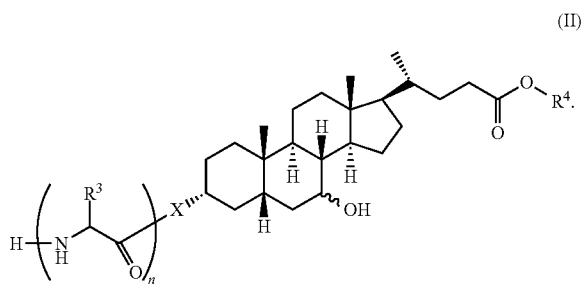

In some embodiments, m is an integer of 1 to 9, an integer of 1 to 8, an integer of 1 to 7, an integer of 1 to 6, an integer of 1 to 5, an integer of 1 to 4, an integer of 1 to 3, an integer of 1 to 2. Each possibility represents a separate embodiment of the invention. In some embodiments, m=1. In other embodiments, m=10.

For m=1, each amino acid in the conjugate represents a separate embodiment of the present invention. Thus, in some embodiments, $R^{1a}$ represents the side chain of arginine. In additional embodiments, $R^{1a}$ represents the side chain of lysine. In additional embodiments, $R^{1a}$ represents the side chain of histidine. In yet additional embodiments, $R^{1a}$ represents the side chain of ornithine.

For m>1, each combination of amino acids in the conjugate represents a separate embodiment of the invention.

In some embodiments, n is an integer of 1 to 9, an integer of 1 to 8, an integer of 1 to 7, an integer of 1 to 6, an integer of 1 to 5, an integer of 1 to 4, an integer of 1 to 3, an integer of 1 to 2. Each possibility represents a separate embodiment of the invention. In some embodiments, n=1. In other embodiments, n=10.

For n=1, each amino acid in the conjugate represents a separate embodiment of the present invention. Thus, in some embodiments, $R^3$ represents the side chain of arginine. In additional embodiments, $R^3$ represents the side chain of lysine. In additional embodiments, $R^3$ represents the side chain of histidine. In yet additional embodiments, $R^3$ represents the side chain of ornithine.

For n>1, each combination of amino acids in the conjugate represents a separate embodiment of the invention.

Non-Limiting Examples of Conjugates:

(1)

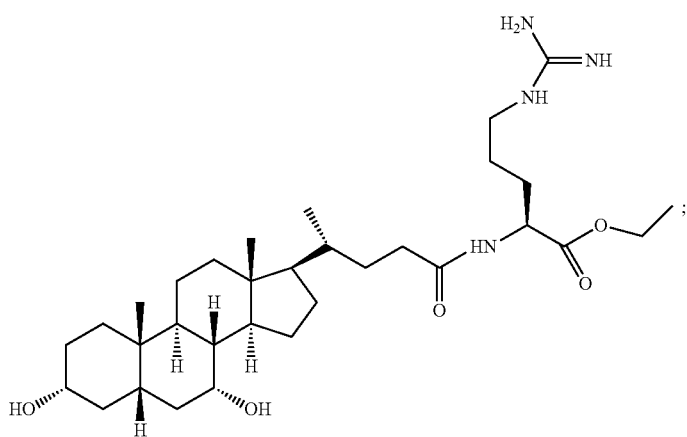

(2)

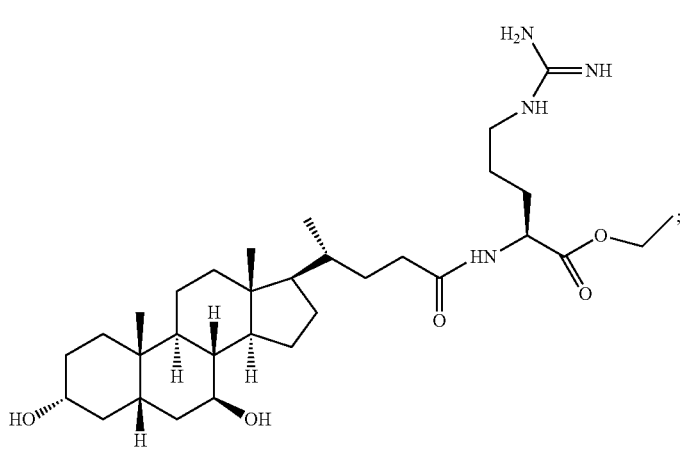

-continued
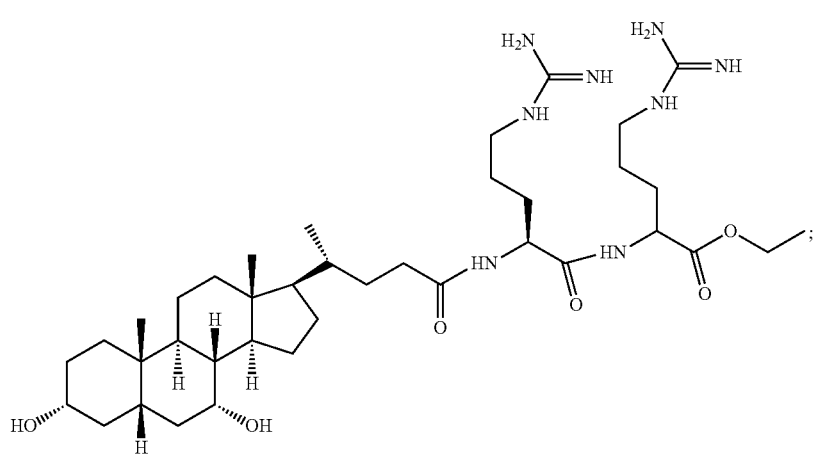
(3)
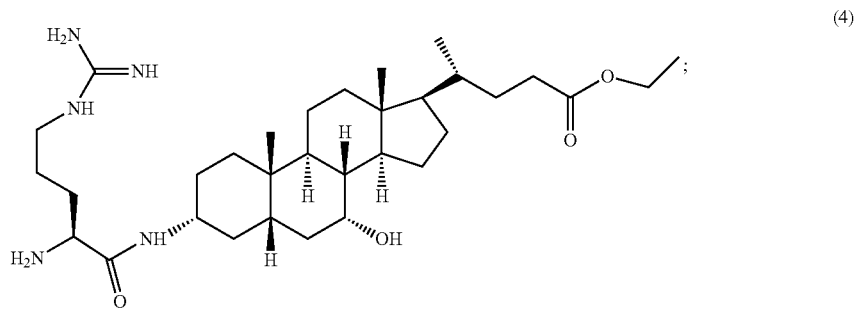
(4)
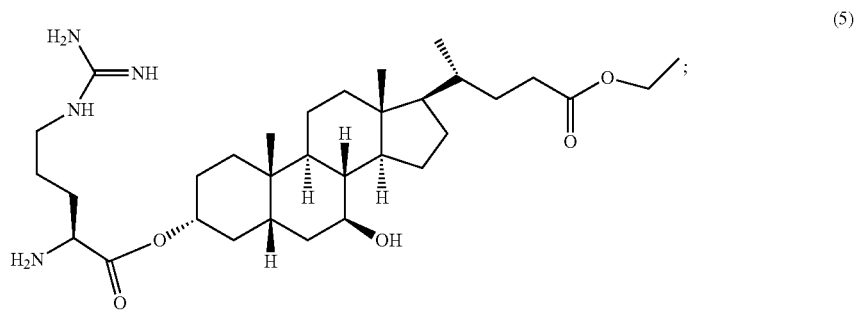
(5)
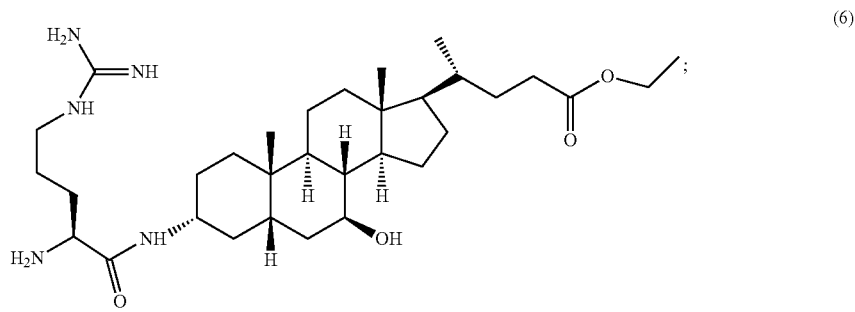
(6)
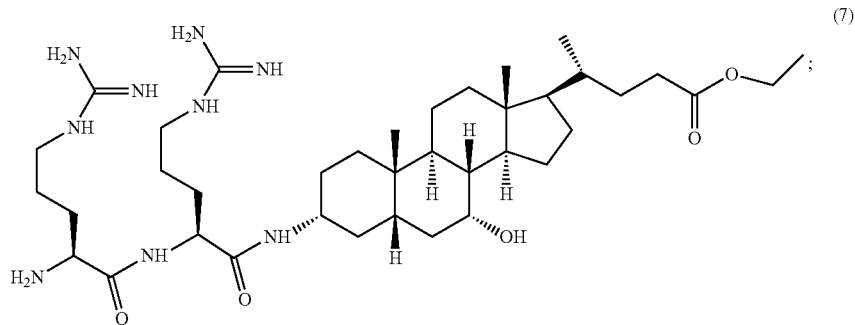
(7)

-continued
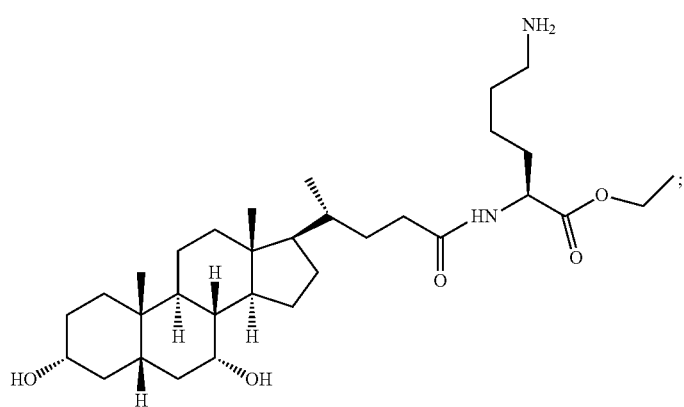
(8)
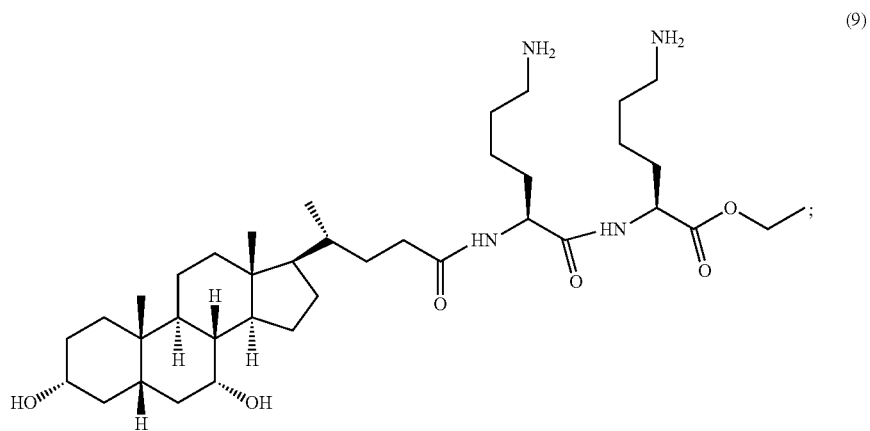
(9)
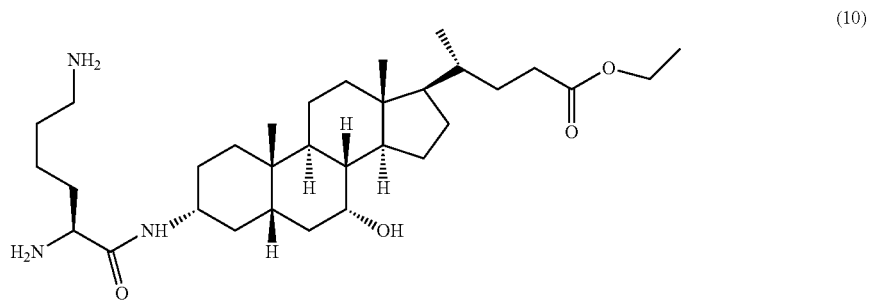
(10)
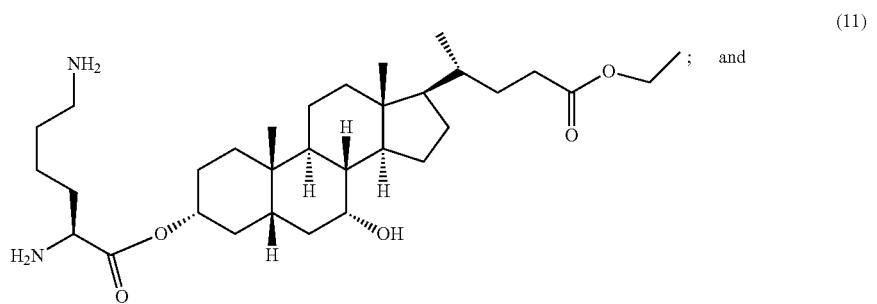
(11) ; and

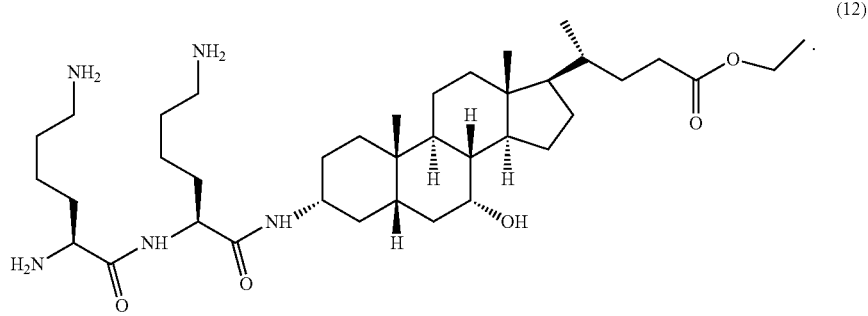

(12)

In some embodiments, conjugates of the present invention have the structure of Formula (IV):

B—Y-A  (IV)

wherein

B represents the residue of a bile acid selected from the group consisting of chenodeoxycholic acid, lithocholic acid, cholic acid, deoxycholic acid, ursodeoxycholic acid, ursocholic acid, hyocholic acid, hyodeoxycholic acid, murocholic acid, dehydrocholic acid, 7-ketodeoxycholic acid, diketocholanic acid, triketocholanic acid, isolithocholic acid, ketolithocholic acid, dehydrolithocholic acid, allocholanic acid, or a salt or ester thereof;

Y represents a linker or is absent; and

A is selected from (i) at least one basic amino acid residue selected from arginine, lysine, histidine and ornithine or a salt or ester thereof; (ii) agmatine or a salt thereof; (iii) a basic amino acid-agmatine moiety; and (iv) a moiety of agmatine-basic amino acid chain.

"A basic amino acid-agmatine moiety" refers to a moiety containing a basic amino acid linked to agmatine. Typically, the amino acid is linked to the bile acid at the N-terminus of the amino acid (through the C-24 carboxyl of the bile acid), and to the agmatine via the C-terminus of the amino acid, through an amine group of the agmatine.

"A moiety of agmatine-basic amino acid chain" refers to a moiety containing a chain of basic amino acids linked to agmatine via the last amino acid of the chain (at the C-terminus of the chain). Typically, the first amino acid of the chain is linked to the bile acid via the N-terminus of the amino acid (through the C-24 carboxyl of the bile acid), and to another amino acid at its C-terminus. The last amino acid of the chain is linked to the agmatine via the C-terminus of the bile acid (through an amine group of the agmatine).

In some embodiments, A is selected from (i) at least one basic amino acid residue selected from arginine, lysine, histidine and ornithine or a salt or ester thereof; and (ii) agmatine or a salt thereof.

Each possibility of B and/or of Y and/or of A represents a separate embodiment of the present invention.

When present, the linker Y comprises two functional groups. The first functional group is capable of forming a bond to the bile acid and the second functional group is capable of forming a bond to the amino acid. In some embodiments, when agmatine is conjugated to the bile acid through a linker, the second functional group of the linker is capable of forming a bond to agmatine. When the linker is absent, the bile acid is linked directly to the amino acid. In some embodiments, when agmatine is used and the linker is absent, the bile acid is linked directly to agmatine. Each possibility represents a separate embodiment of the present invention.

Suitable linkers (if present) include compounds of the formula $M^1$-Z-$M^2$ wherein $M^1$ is a functional group capable of bonding to the bile acid, $M^2$ is a functional group capable of bonding to the amino acid moiety, and Z is a hydrocarbon chain (e.g., C1-C6 alkylene, $C_2$-$C_6$ alkenylene and the like). The nature of the functional groups $M^1$ and $M^2$ will depend on the type of link made to the amino acid or bile acid. Examples of $M^1$ and $M^2$ moieties include, but are not limited to $NH_2$, OH, acid chloride, acid anhydride and sulfonyls.

The bile acid can be linked to the amino acid or agmatine (either directly or indirectly through the linker) through available hydroxyl or carboxyl groups. For example, when the bile acid is chenodeoxycholic acid or ursodeoxycholic acid, the conjugation of the bile acid to the amino acid can occur through the hydroxyl groups at C-3, C-7, or through the 24-carboxyl group of the bile acid. Each possibility represents a separate embodiment of the present invention.

The amino acid moiety can be linked to the bile acid (either directly or indirectly through the linker) through the alpha-amine, carboxyl, or side chain of said amino acid. Each possibility represents a separate embodiment of the present invention.

Agmatine can be linked to the bile acid (either directly or indirectly through the linker) through its amine or guanidine groups.

Pharmaceutical Compositions

Pharmaceutical compositions according to embodiments of the present invention comprise a bile acid-basic amino acid conjugate as an active ingredient. According to some embodiments, pharmaceutical compositions of the present invention comprise a bile acid-agmatine conjugate as an active ingredient. In some embodiments, the pharmaceutical compositions are for use in the treatment of at least one undesired symptom of, or diseases and disorders related to, the metabolic syndrome.

As used herein, the terms "active ingredient" and "active agent" are used interchangeably and refer to a component that has a pharmacological activity.

In some embodiments, the conjugate in the pharmaceutical compositions is a compound of Formula (Ia), Formula (Ib), Formula (Ic) or Formula (II). Each possibility represents a separate embodiment of the present invention.

In some embodiments, the conjugate in the pharmaceutical compositions is a compound of Formula (III).

In some embodiments, the conjugate in the pharmaceutical compositions is a compound of Formula (IV).

In some embodiments, the conjugate in the pharmaceutical compositions is selected from the group consisting of compound (1), compound (2), compound (3), compound (4), compound (5), compound (6), and compound (7) and salts thereof.

In some embodiments, a conjugate as described herein is the only active ingredient present in the pharmaceutical composition. Thus, in some embodiments, a pharmaceutical composition is provided, consisting essentially of a conjugate as described herein as the sole active ingredient. It is to be understood that according to these embodiments, the pharmaceutical composition does not contain additional active agents, particularly active agents that are supported and/or in need of the bile acid-basic amino acid conjugates for their activity and/or delivery. For example, pharmaceutical compositions according to these embodiments do not contain a therapeutically active protein, e.g., insulin. It is further to be understood that according to these embodiments, non-active ingredients are included in the pharmaceutical composition. In some embodiments, pharmaceutically acceptable excipients and carriers are included in the composition. Pharmaceutical compositions of the present invention are preparations of the active ingredient with one or more acceptable excipients. The purpose of a pharmaceutical composition is to facilitate administration of the active ingredient to an organism.

As used herein, the term "pharmaceutically acceptable", when referring to a substance or agent, such as a carrier or an excipient, refers to a substance that does not cause significant irritation to an organism and does not abrogate the biological activity and properties of the administered active agent.

The active ingredient is present in the compositions of the present invention in a therapeutically effective amount, effective to achieve the intended purpose, for example, in an amount effective to treat a certain disease. Determination of a therapeutically effective amount is well within the capability of those skilled in the art, and may include standard clinical techniques, in vitro assays and animal assays.

The compositions of the present invention are typically formulated for systemic administration, particularly oral administration. Non-limiting examples of formulations for oral administration include tablets, pills, dragees, capsules, liquids, gels, syrups, slurries and suspensions, for oral ingestion by a patient.

Solid formulations may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release.

Liquid formulations include aqueous solutions, with or without organic co-solvents, aqueous or oil suspensions, flavored emulsions with edible oils, as well as elixirs and similar pharmaceutical vehicles.

The compositions of the present invention may also be formulated for other routes of administration, including for example, rectal, intravenous, intramuscular, intradermal, subcutaneous and intranasal administration, as known in the art.

In some embodiments, the composition comprises at least one additive useful in the pharmaceutical fields, including, but not limited to fats, emulsifiers and co-emulsifiers, hydrophilic or lipophilic gelling agents, colorants, fragrances, emollients, humectants, preservatives, vitamins, chelators, solvents, fillers, thickeners, hydrophilic and lipophilic filters, dyestuffs, neutralizers, penetration-enhancing agents and polymers.

The quantities and concentrations of these various additives are those conventionally used in pharmaceutical preparations as is known to a person skilled in the art. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000).

Methods and Uses

According to an aspect of the present invention, there is provided herein methods for treating diseases or disorders associated with the metabolic syndrome in a subject in need thereof. The methods disclosed herein comprise administering to the subject a bile acid-basic amino acid conjugate, or a pharmaceutical composition comprising a bile acid-basic amino acid conjugate as an active ingredient and a pharmaceutically acceptable excipient. According to some embodiments, the methods disclosed herein comprise administering to the subject a pharmaceutical composition comprising a bile acid-agmatine conjugate as an active ingredient, and a pharmaceutically acceptable excipient.

As noted above, the metabolic syndrome is a collection of several clinical conditions. There are a few sets of criteria for the diagnosis of the syndrome established by different health organizations, the most widely adopted is the one proposed by the National Cholesterol Education Program (NCEP) Adult Treatment Panel III (ATP III) and later on amended by the American Heart Association (AHA) and the National Heart Lung and Blood Institute (NHLBI). According to this set of criteria, the metabolic syndrome is identified by the presence of three or more of the following components: abdominal obesity (waist circumference >102 cm in men, >88 cm in women, with ethnicity-specific modification of the cut-off values), elevated triglycerides (>150 mg/dl or on drug treatment for elevated triglycerides), reduced HDL-cholesterol level (<40 mg/dl in men, <50 mg/dl in women or on drug treatment for reduced HDL-cholesterol), hypertension (systolic blood pressure >130 mmHg or diastolic blood pressure >85 mm Hg or on antihypertensive drug treatment) and impaired fasting glucose (100-125 mg/dl or on antidiabetic drug treatment).

As used herein, "treating" and "treatment", refers to reduction, amelioration or even elimination of at least some of the symptoms associated with a particular disease or disorder related to the metabolic syndrome. For example, the terms may include at least one of reducing body weight, and inhibiting or preventing body weight gain. Each possibility represents a separate embodiment of the invention. In some embodiments, treatment includes inhibiting or preventing body weight regain of body weight previously lost (e.g., as a result of diet, exercise, or pharmacotherapy).

Treatment may also include lowering the blood level of at least one of triglycerides, total cholesterol, LDL-cholesterol and circulating free fatty acid. Each possibility represents a separate embodiment of the invention. Treatment may also include increasing the blood level of HDL-cholesterol. Treatment may also include balancing the level of one or more lipids in the blood and maintaining a balanced level of lipids in the blood.

Treatment may also include at least one of lowering the level of glucose in the blood (fasting glucose, following a glucose tolerance test, or both), balancing the level of glucose in the blood and maintaining a balanced level of glucose in the blood.

Treatment may also include reducing or inhibiting fat accumulation in the liver.

Treatment may also include at least one of lowering blood pressure, balancing the blood pressure and maintaining a balanced blood pressure.

The term "level" as used herein refers to the amount of a certain substance contained in a sample (e.g., blood or a tissue). Typically, the term refers to the concentration of a certain substance in a sample (for example, amount in mg per unit volume of blood, such as mg per milliliter, or mg per deciliter).

As used herein, the terms "reducing", "decreasing" and "lowering", when referring to a level of a certain substance or to a measureable index such as body mass, are intended to refer to reduction compared to an initial level, prior to treatment with the conjugates described herein. Similarly, the term "increasing" is intended to refer to an increase compared to an initial level, prior to treatment with the conjugates described herein.

As used herein, the terms "balancing" and "balanced", when referring to a level of a certain substance, are intended to describe a level that is within the normal range, that is considered healthy, as known in the art.

As used herein, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

In some embodiments, treatment encompasses delaying or even preventing the onset of complications related to a particular condition. In some embodiments, treatment encompasses delaying or even preventing the progression from pre-diabetes to type-2 diabetes. In additional embodiments, treatment encompasses delaying or even preventing the progression from steatosis to steatohepatitis.

The compositions and methods of the present invention are typically employed for the treatment of a mammal, preferably a human In some embodiments, the disease or disorder is obesity or excessive weight.

Thus, in some embodiments, a method for treating obesity or excessive weight in a subject in need thereof is provided, the method comprising administering to the subject a pharmaceutical composition comprising a bile acid-basic amino acid conjugate.

In some embodiments, a method for promoting weight loss, inhibiting weight gain or both in a subject in need thereof is provided, the method comprising administering to the subject a pharmaceutical composition comprising as an active ingredient a bile acid-basic amino acid conjugate.

In some embodiments, the method is applied for the prevention of drug-induced weight gain and other drug-induced symptoms of metabolic syndrome. For example, the method may be applied for the prevention of anti-psychotic drugs-induced weight gain, and weight gain caused by steroids. Thus, in some embodiment, a method for treating or preventing drug-induced weight gain is provided, the method comprising administering to the subject a pharmaceutical composition comprising as an active ingredient a conjugate as described herein, of a bile acid with basic amino acid(s) or with agmatine herein.

In some embodiments, the disease or disorder is dyslipidemia. In some embodiments, the dyslipidemia is mixed dyslipidemia, wherein the level of more than one type of lipid deviates from its normal range. A subject with dyslipidemia may be identified by, for example, by measuring blood lipid levels, e.g., fasting blood lipid levels, using methods routine to one of skill in the art. In some embodiments, non-HDL cholesterol is measured, e.g., the amount of total cholesterol minus the amount of HDL cholesterol.

In some embodiments, a method for lowering the level of at least one of triglycerides, total cholesterol, LDL-cholesterol and circulating free fatty acid in the blood of a subject in need thereof is provided, the method comprising administering to the subject a pharmaceutical composition comprising as an active ingredient a bile acid-basic amino acid conjugate.

In some embodiments, the disease or disorder is pre-diabetes. In other embodiments, the disease or disorder is type-2 diabetes. In yet other embodiments, the disease or disorder is hyperglycemia.

In some embodiments, a method for lowering the level of glucose in the blood of a subject in need thereof is provided, the method comprising administering to the subject a pharmaceutical composition comprising as an active ingredient a bile acid-basic amino acid conjugate. In some embodiments, a method of maintaining a balanced level of glucose in the blood of a subject in need thereof is provided.

In some embodiments, the disease or disorder is a fatty liver disease. In some embodiments the fatty liver disease is steatosis. In other embodiments, the fatty liver disease is nonalcoholic steatohepatitis (NASH).

In some embodiments, a method for reducing or inhibiting fat accumulation in the liver of a subject in need thereof is provided, the method comprising administering to the subject a pharmaceutical composition comprising as an active ingredient a bile acid-basic amino acid conjugate.

In some embodiments, the disease or disorder is hypertension. In some embodiments, a method for lowering blood pressure of a subject in need thereof is provided, the method comprising administering to the subject a pharmaceutical composition comprising as an active ingredient a bile acid-basic amino acid conjugate. In some embodiments, a method of maintaining a balanced blood pressure of a subject in need thereof is provided.

The methods of the present invention typically comprise systemic administration of the pharmaceutical composition, particularly oral administration.

The exact formulation, route of administration, and dosage can be chosen by a practitioner based on each patient's circumstances. Exemplary, non-limiting dosages can range from about 1 to 50 mg/kg/day, for example between about 5-10 mg/kg/day to about 10-20 mg/kg/day.

In some embodiments, the pharmaceutical composition comprising the conjugate is administered immediately before or immediately after a meal. In some embodiments, the pharmaceutical composition is administered with a meal.

The administration schedule can be taken once-daily, twice-daily, thrice-daily, once-weekly, twice-weekly, thrice-weekly, or any other administration schedule known to those of skill in the art.

The methods of the present invention may be combined with one or more known treatments of the above described disorders/diseases.

In some embodiments, the present invention provides the use of conjugates as described herein, for the manufacture of a medicament for the treatment of a medical condition associated with the metabolic syndrome.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Synthesis of Chenodeoxycholyl-Arginine-Ethyl Ester (CDCArg)

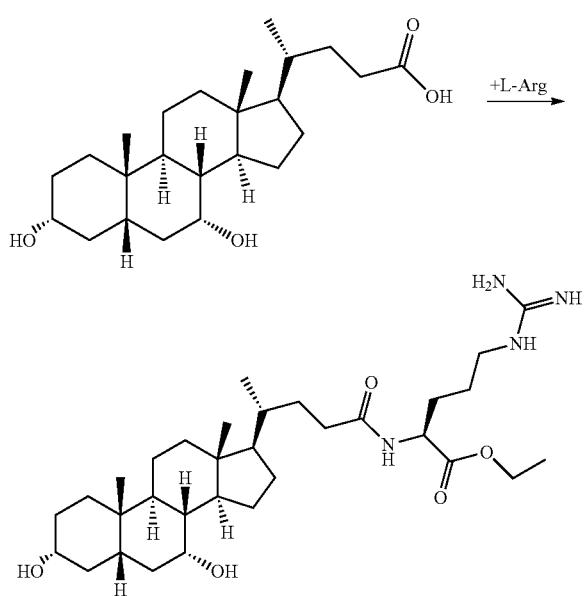

Synthetic Procedure:
1. Chenodeoxycholic acid (78.5 gm, 0.2 mol) was dissolved in DMF (250 mL) and tributylamine (95.3 mL) in 1000 ml round bottom flask.
2. Ethyl chloroformate (20.16 mL) was slowly added to the mixture at 0° C.
3. The mixture was stirred at 0° C. for 30 min.
4. In 500 ml round bottom flask, a mixture of arginine ethyl ester dihydrochloride (60.28 gm, 0.22 mol) and tributylamine (95.3 mL) in DMF (200 mL) was prepared.
5. It was transferred to a dropping funnel and slowly added to the mixture of mixed anhydride prepared from chenodeoxycholic acid and ethyl chloroformate at 0° C. (step 1).
6. The mixture was stirred at room temperature for overnight.
7. The mixture was poured on ice and the gummy residue separated out was collected by separating from water (77 gm).
8. The water from step 5 concentrated on rotary evaporator.
9. The residue obtained after concentration was loaded above the silica gel bed (300 gm) and eluted with methylene chloride followed by methanol-methylene chloride (1:4).
10. The earlier fractions with 100% methylene chloride were discarded since they mostly contained impurities and solvents (i.e. DMF and tri-butylamine).
11. The later fractions were concentrated and provided a gummy residue (45 gm).
12. The crude product from step 7 (77 gm) and step 11 (45 gm) was dissolved in methanol and combined.
13. It was then purified on the Teledyne Isco 330 gm silica gel column using 10-15% methanol-methylene chloride. The purification was carried out on Combi-Flash using the ELSD detector.
14. Three separations runs were performed. The pure fractions were collected and concentrated on rotary evaporator to give chenodeoxycholyl-arginine-ethyl ester (CDCArg) (50.8 gm).

Reaction was repeated following the above procedure.
LC-ELSD and MS data indicated that the purity of the compound is 97% or greater.

Example 2—Testing CDCArg in a High Fat Diet (HFD) Model in Mice

Experimental Design

HFD: 60% calories from fat (mainly palm stearin).
Control diet: low fat diet (LFD) 16% calories from fat (vegetable oil, regular animal diet).
C57BL mice mail, 8 mice per group.
Treatment Groups:
1) Animals supplemented with control LFD ("LFD" or "Control").
2) Animals supplemented with HFD ("HFD").
3) Animals supplemented with HFD and CDCArg in an amount that equals 0.5% of the food ("HFD+CDCArg").
4) Animal supplemented with HFD and cholic acid in an amount that equals 0.5% of the food ("HFD+CA").
5) Animal supplemented with HFD and 1.25% L-arginine in the drinking water ("HFD+Arg").

The animals in the different groups were fed the different diets for five weeks, during which their food consumption and various physiological parameters were measured. Chemistry (cholesterol and triglycerides, electrolytes and creatinine) and enzymatic blood measurements were performed using a chemical analyzer and commercial kits. Leptin and insulin levels were detected using a luminex assay kit (Millipore, Israel). Blood glucose was measured by Optium Xceed™ (Abbott) glucometer.

For liver histology, animals were sacrificed and liver tissues were removed and fixed in 4% formalin at room temperature. Liver sections were subjected to Hematoxylin-Eosin staining (PathoVet Veterinary Pathology Services, Rehovot, Israel).

Statistical analysis was performed using one way ANOVA and post HOC test Fisher's least significant difference test for experiments with multiple groups. Differences were considered significant at $P<0.05$. Other types to statistical tests when used are indicated in the figure legends.

Results

Average Food Consumption:

The animal food was weighted during the experiment, and food consumption was calculated at the beginning of each week. The results are summarized in FIG. 1. Results represent average daily consumption of food of weeks 2, 3, 4 and 5. Means with different letters are statistically different, $P<0.05$. (one way ANOVA, Post Hoc LSD test). As can be seen in the figure, significantly increased food consumption was observed in the group of mice fed a HFD+CA compared to mice fed a control diet, HFD and HFD+Arg, and even more in the group of mice fed a HFD+CDCArg.

Average Body Weight:

Animals' body weight was measured during the experiment at the beginning of each week. The results are summarized in FIG. 2. Repeated measurements of weight indicated with different letters are statistically different, P<0.05 (one way ANOVA, Post Hoc LSD test). As can be seen in the figure, all groups showed an increase in body weight during the experiment. As expected, the lowest increase in body weight was observed in the group of mice fed a control, low fat diet. Among the groups of mice that consumed a high fat diet, it was surprisingly found that mice fed a HFD+CDCArg showed the lowest increase in body weight, despite a significantly increased food consumption.

Average Weight of Adipose Tissue (Testicular Fat):

Measurements were carried out at the end of week 5. The results are summarized in FIG. 3. Means with different letters are statistically different, P<0.05 (one way ANOVA, Post Hoc LSD test). As can be seen in the figure, HFD resulted in an increase in the weight of testicular fat in all groups of mice that consumed this diet compared to mice that consumed the control diet. However, consumption of HFD+CDCArg and HFD+CA showed a significantly lower increase in testicular fat weight compared to consumption of HFD alone or HFD+Arg.

Figure 2:
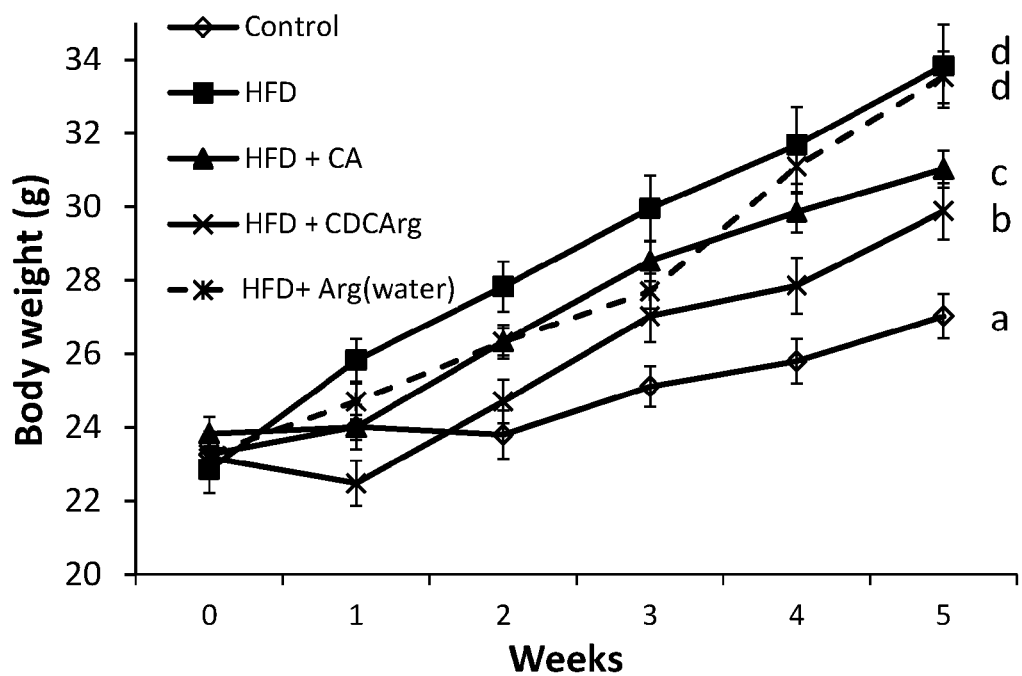
FIG. 2. Average body weight changes during a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HFD+Arg). Repeated measurements of weight indicated with different letters are statistically different, P<0.05 (one way ANOVA, Post Hoc LSD test).
Figure 3:
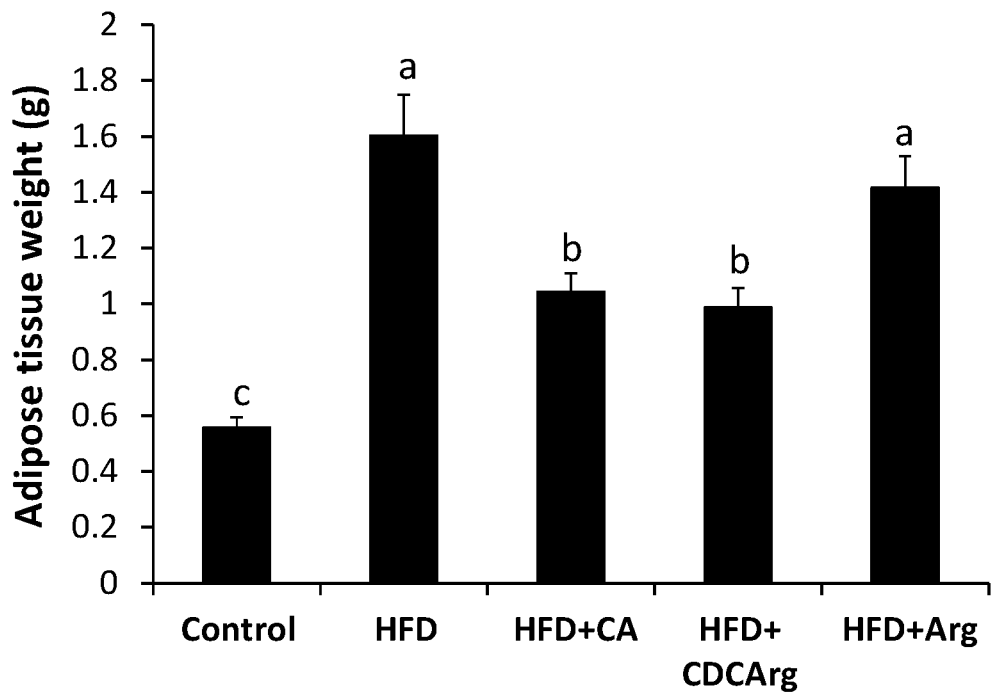
FIG. 3. Average weight of adipose tissue (testicular fat) following a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HFD+Arg). Means with different letters are statistically different, P<0.05 (one way ANOVA, Post Hoc LSD test).

Altogether, the results shown in FIGS. 1-3 demonstrate anti-obesity properties of CDCA.

Plasma Lipid Profile:

Average Total Cholesterol in the Blood:

Measurements were carried out at the end of week 5. The results are summarized in FIG. 4. Means with different letters are statistically different, P<0.05 (one way ANOVA, Post Hoc LSD test). As can be seen in the figure, despite the consumption of a HFD, mice supplemented with CDCArg showed a similar level of total blood cholesterol to that of mice fed a control, low fat diet Similar results were observed for mice fed a HFD+CA. This in contrast to mice fed a HFD alone and HFD+Arg, who showed significantly increased levels of total blood cholesterol at the end of the five-week experiment compared to control.

Figure 5A:
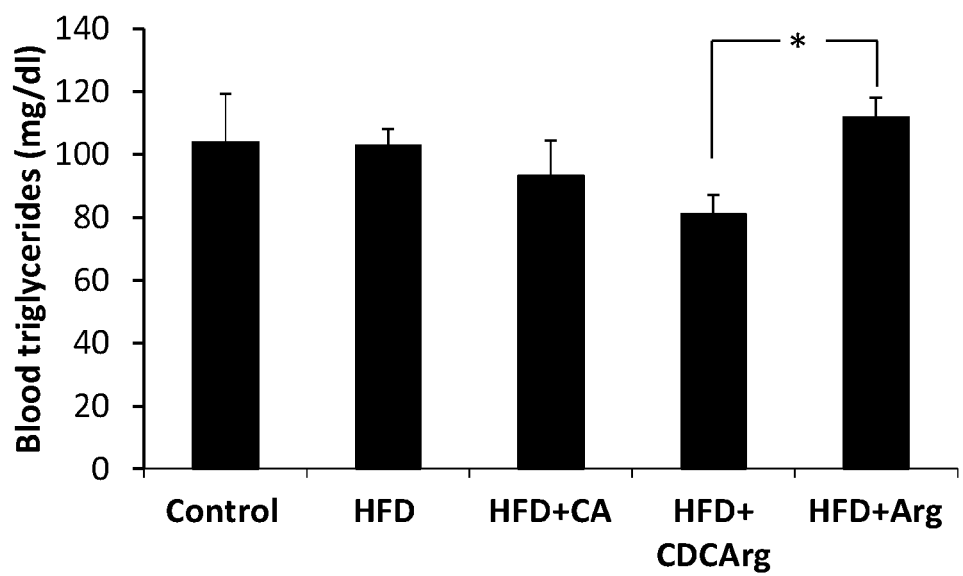
FIG. 5. (A) Average triglycerides in the blood following a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HF+Arg). Means marked with an asterisk * are statistically different, P<0.05 (one way ANOVA, Post Hoc LSD test); (B) Toxicity effects indicated by electrolyte balance in the blood and renal function. Mice were fed for 5 weeks with LFD, HFD, HFD+CA, HFD+CDCArg or HFD+Arg (ad libitum). Top left panel—average plasma creatinine levels, rest of the panels—average plasma electrolytes (sodium, potassium and chloride) levels.

Average Triglycerides in the Blood:

Measurements were carried out at the end of week 5. The results are summarized in FIG. 5a. Means marked with an asterisk * are statistically different, P<0.05 (one way ANOVA, Post Hoc LSD test). As can be seen in the figure, similar levels of triglycerides in the blood were observed in all groups of mice, except for the HFD+Arg group who showed a higher level of blood triglycerides compared to the HFD+CDCArg group.

Figure 5B:
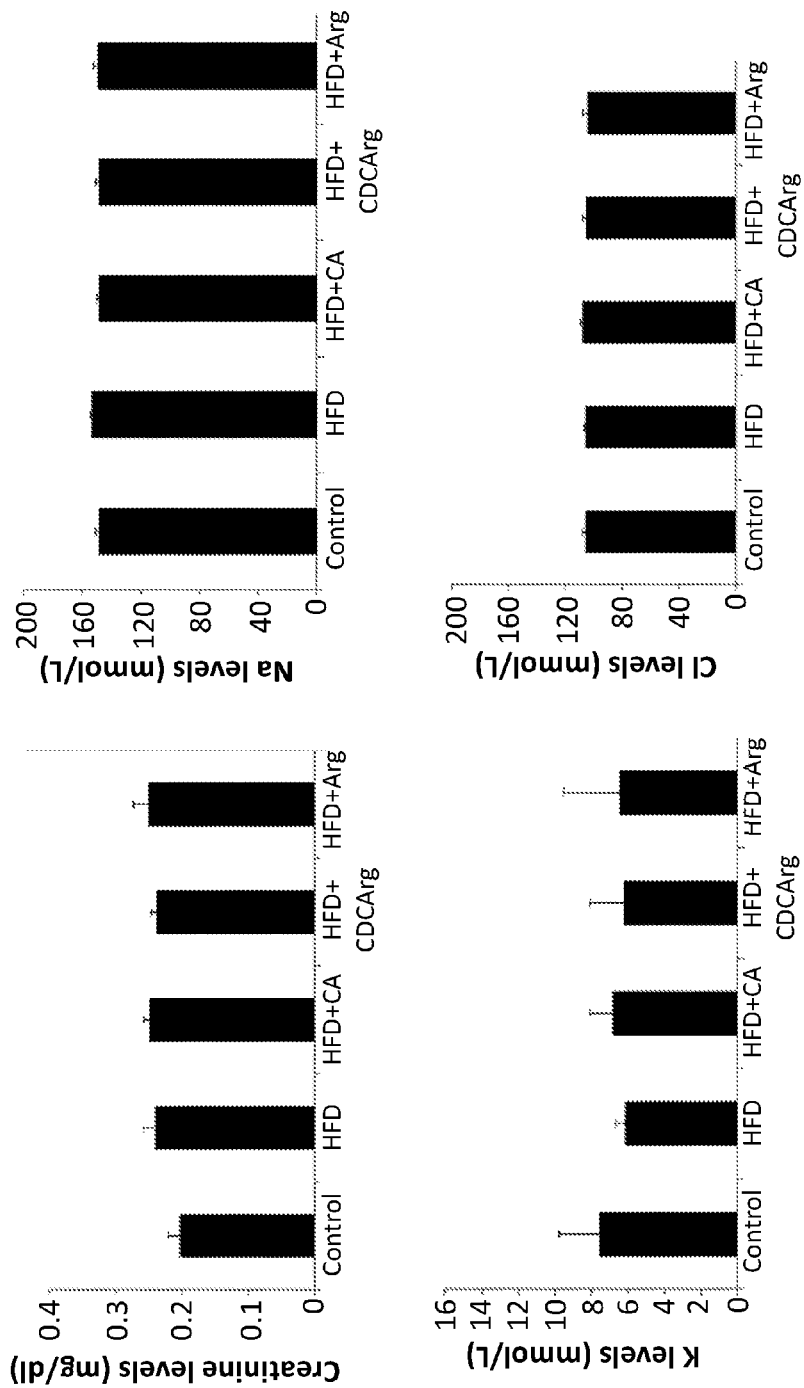

The general toxicity, indicated by electrolyte balance and renal function measured by plasma creatinine, sodium, potassium and chloride levels, was not significantly different between the groups, indicating no acute toxicity of the diet treatments (FIG. 5b).

Figure 4:
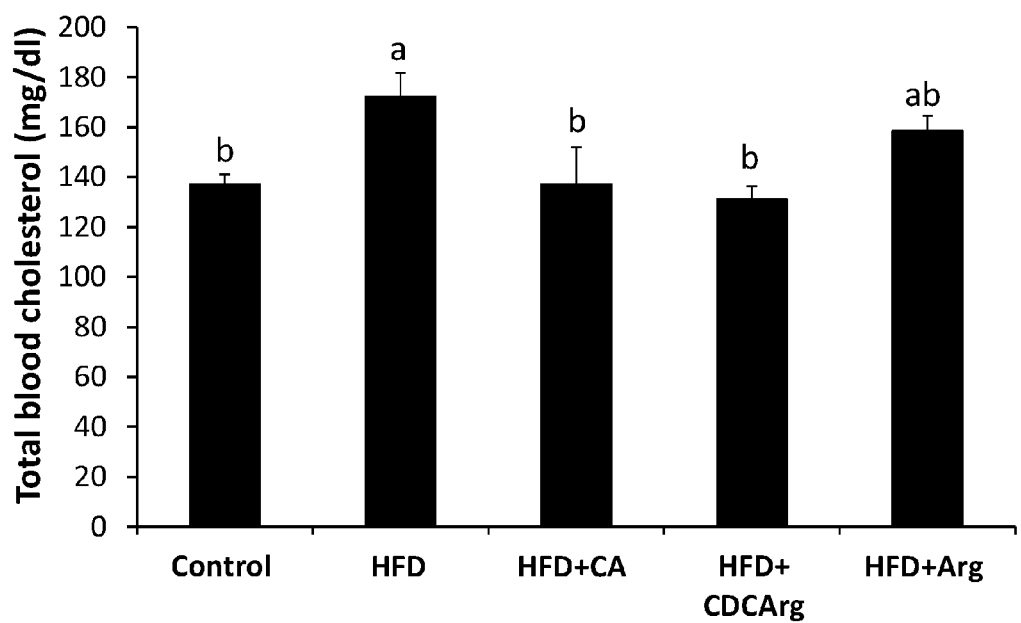
FIG. 4. Average total cholesterol in the blood following a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HFD+CA) and high fat diet plus L-arginine in the drinking water (HFD+Arg). Means with different letters are statistically different, P<0.05 (one way ANOVA, Post Hoc LSD test).

Altogether, the results shown in FIGS. 4-5 demonstrate anti-dyslipidemic properties of CDCArg, without toxicity effects.

Figure 6A:
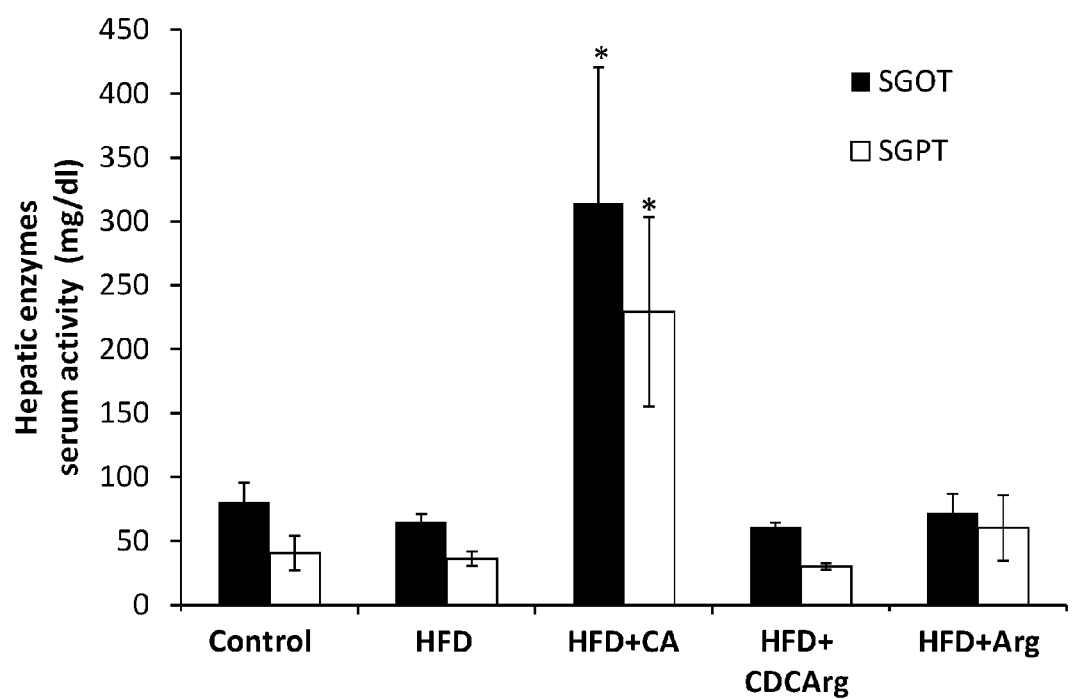
FIG. 6. Average blood hepatic enzyme activity ((A)—SGOT, SGPT; (B)—Alkaline phosphatase) following a five-week experiment of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HF+CA) and high fat diet plus L-arginine in the drinking water (HFD+Arg). Means marked with an asterisk * are statistically different, P<0.05 (one way ANOVA, Post Hoc LSD test).
Figure 6B:
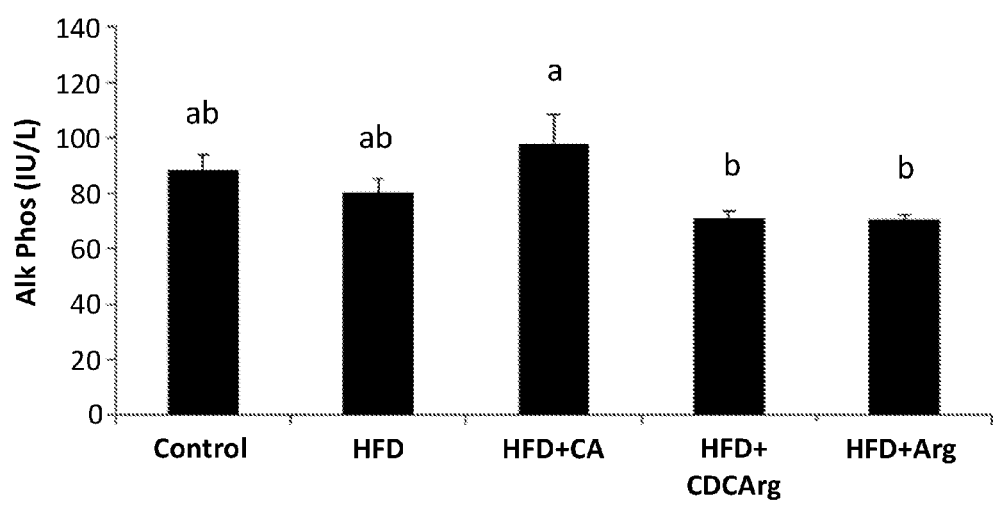

Average Blood Hepatic Enzyme Activity (SGOT, SGPT, Alkaline Phosphatase):

Measurements were carried out at the end of week 5. The results are summarized in FIG. 6a-b. Means marked with an asterisk * are statistically different, P<0.05 (one way ANOVA, Post Hoc LSD test). As can be seen in FIG. 6a, a significant increase in the level of the hepatic enzymes SGOT and SGPT in the blood was observed in the group of mice fed a HFD supplemented with CA compared to all other groups. Unlike CA, CDCArg did not potentiate saturated fat-induced liver damage Alkaline phosphatase levels in the blood were not significantly elevated in any of the treatments, suggesting that CA is mainly toxic to hepatocytes and less to cholingiocytes in the liver (FIG. 6b).

Figure 7:
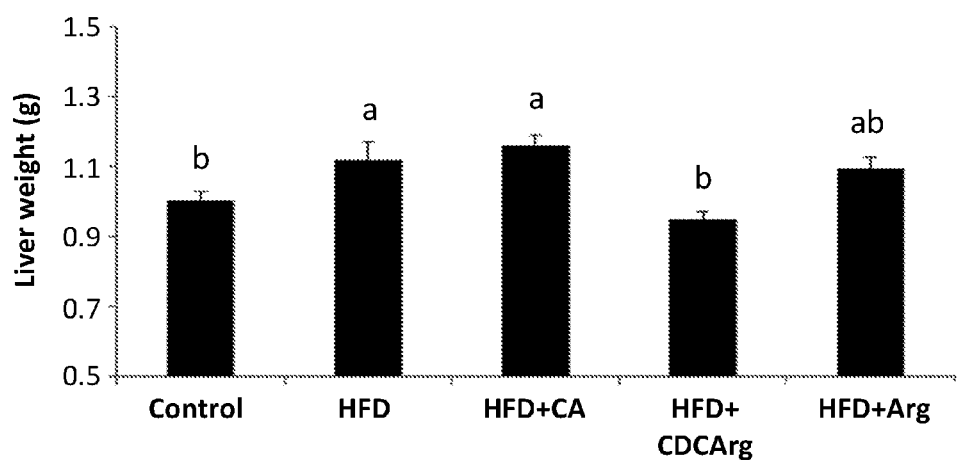
FIG. 7. Average liver weight following a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HFD+Arg). Means marked with an asterisk * are statistically different, P<0.05 (one way ANOVA, Post Hoc LSD test).

Average Liver Weight:

Hepatomegaly (enlarged liver) can occur as a result of several causes including infection/inflammation and metabolic disorders. For example, accumulation of lipids in the liver can lead to increased liver weight. Measurements were carried out at the end of week 5. The results are summarized in FIG. 7. Means marked with an asterisk * are statistically different, P<0.05 (one way ANOVA, Post Hoc LSD test). As can be seen in the figure, liver weight was found to increase significantly following consumption of HFD and HFD+CArg compared to consumption of the control diet. In contrast, HFD+CDCArg showed no difference in liver weight compared to control. Thus, the results shown in FIG. 7 support the use of CDCArg in the treatment of non-alcoholic fatty liver disease.

Figure 8A:
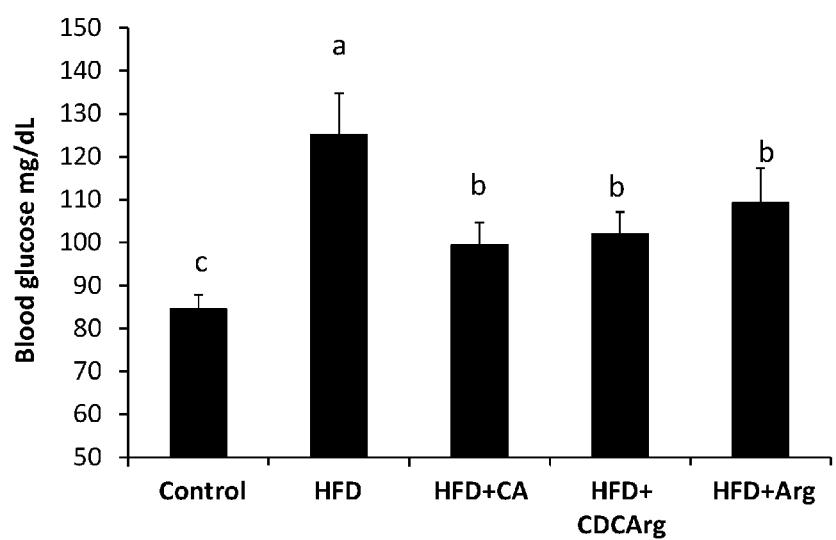
FIG. 8. Average blood (A) glucose, (B) insulin and (C) leptin following a five-week experiment, of mice fed a high fat diet plus chenodeoxycholyl-arginine-ethyl ester (HFD+CDCArg) versus mice fed a control low fat diet (Control), high fat diet with no other supplements (HFD), high fat diet plus cholic acid (HFD+CA) and high fat diet plus L-arginine in the drinking water (HFD+Arg). Means with different letters are statistically different, P<0.05 (one way ANOVA, Post Hoc LSD test).

Blood Glucose:

Measurements were carried out at the end of week 5. The results are summarized in FIG. 8a. Means with different letters are statistically different, P<0.05 (one way ANOVA, Post Hoc LSD test). As can be seen in the figure, a significant increase in the level of glucose in the blood was observed in the group of mice that consumed a HFD. In contrast, mice fed a HFD supplemented with CDCArg showed a similar level of blood glucose to that of mice fed the control diet Similar results were observed for mice fed a HFD+CA. Thus, the results shown in FIG. 8 support the use of CDCArg in the treatment of diabetes, particularly type II diabetes.

Figure 8B:
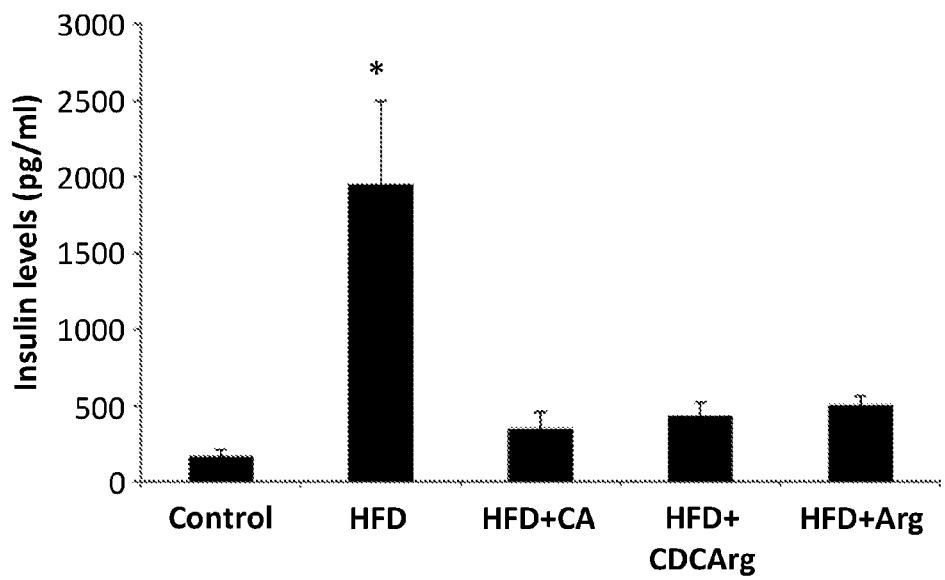
Figure 8C:
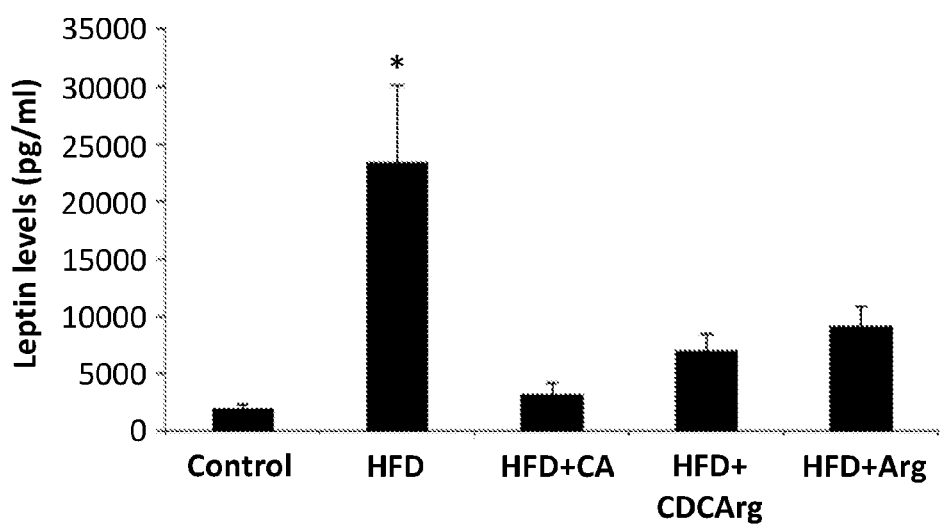

Plasma Insulin and Leptin:

As can be seen in FIGS. 8b-c, plasma level of insulin and leptin were significantly decreased in the HFD+CDCArg group compared to the HFD group Similar results were observed for HFD+CA.

Figure 9:
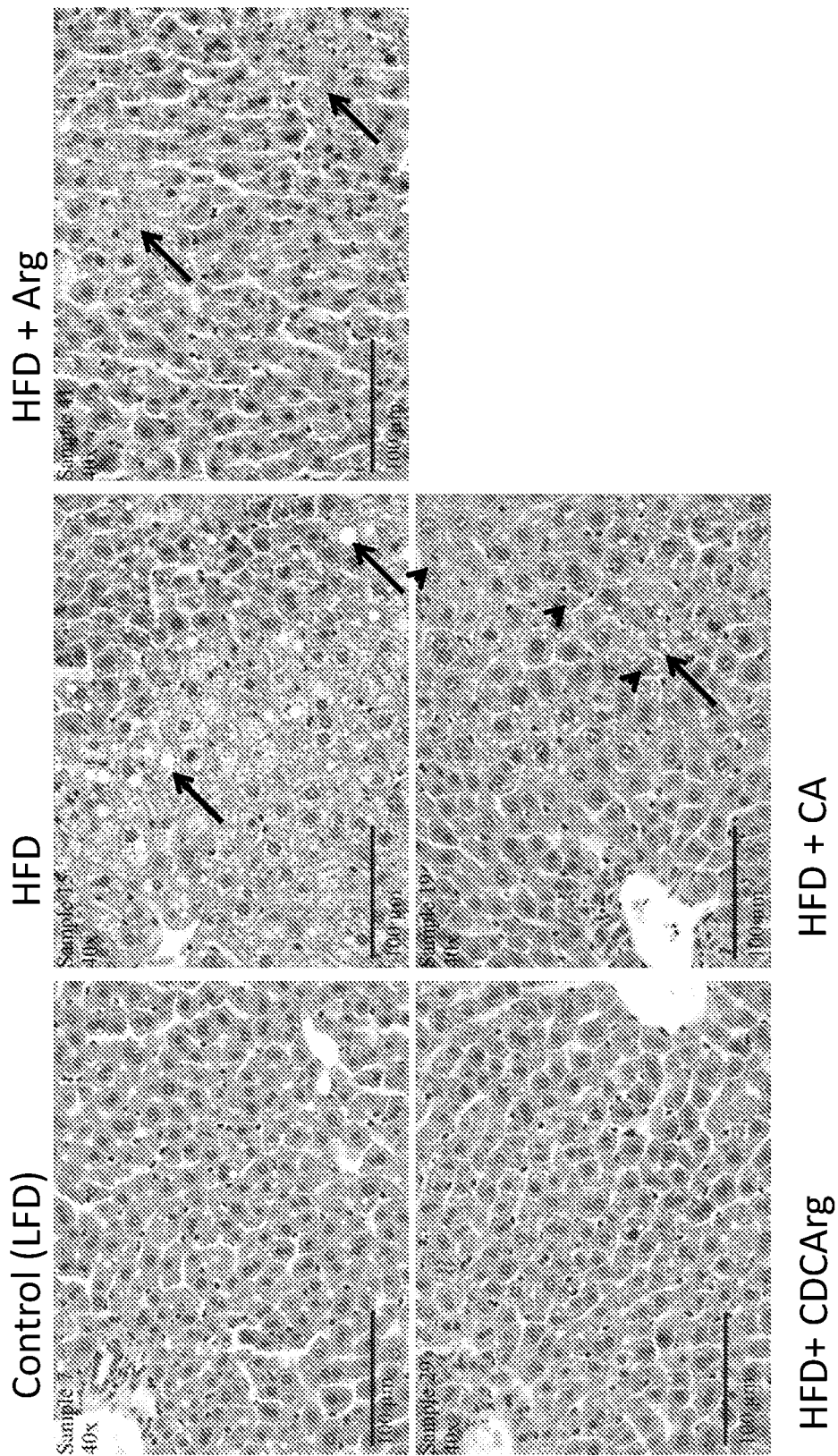
FIG. 9. Histological evaluation of livers by H&E staining (magnification 400×). Animals were treated with high fat diet (HFD) with and without different compounds. Arrows indicate micro and macrovesicular steatosis. Arrow heads indicate hepatocytes balooning. HFD=high fat diet, LFD=low fat diet, CDCArg=chenodeoxycholyl-arginine-ethyl ester, CA=cholic acid.

Evaluation of Liver Damage by Histology:

Histological evaluation of livers was performed by H&E staining at the end of week 5. Exemplary staining of liver sections obtained from mice fed with the different diets is shown in FIG. 9. In the figure, arrows indicate micro and macrovesicular steatosis, and arrow heads indicate hepatocyte ballooning. As can be seen in the figure, staining of livers obtained from mice fed a HFD supplemented with CDCArg was similar to that of mice that consumed the control diet. In contrast, increased liver damage was detected in livers obtained from mice fed a HFD alone and HFD+CA/Arg. Comparing the histological features of CA with CDCArg showed a major difference between these treatments on parameters affected by liver damage and hepatocyte injury. In the HFD+CA treated group, a massive hepatocyte necrosis was observed. This histological observation was in correlation with the elevated levels of blood liver enzymes SGOT and SGPT described above.

Table 1 summarizes scoring of liver sections that was performed according to Modified Brunt Criteria of Staging and Grading NAFLD (non alcoholic fatty liver disease) taken from Huang et al, Am J Gastroenterol 2005; 100:1072-1081, as described in Table 2 below.

TABLE 1

Scoring of liver sections

| Liver section | Steatosis | Ballooning and disarray | Inflammation intra-acinar | Portal inflammation | Fibrosis | Total |
| --- | --- | --- | --- | --- | --- | --- |
| C | 1 | 0 | 0 | 0 | 0 | 1 |
| C | 2 | 0 | 1 | 1 | 0 | 4 |
| HFD | 3-4 | 0 | 1 | 1 | 0 | 5-6 |

TABLE 1-continued

Scoring of liver sections

| Liver section | Steatosis | Ballooning and disarray | Inflammation intraacinar | Portal inflammation | Fibrosis | Total |
|---|---|---|---|---|---|---|
| HFD | 3 | 0 | 0 | 1 | 0 | 4 |
| HFD | 2 | 0 | 1 | 1 | 0** | 4 |
| HFD | 3-4 | 0 | 1 | 1 | 0 | 5-6 |
| HFD + CA | 3 | 1* | 3 | 1 | 0** | 8 |
| HFD + CA | 2 | 0* | 0 | 1 | 0 | 3 |
| HFD + CA | 1 | 0 | 0 | 0 | 0 | 1 |
| HFD + CA | 0 | 0* | 0 | 2 | 0** | 2 |
| HFD + CDCArg | 0 | 0 | 0 | 0 | 0 | 0 |
| HFD + CDCArg | 1 | 0 | 0 | 0 | 0 | 1 |
| HFD + CDCArg | 1 | 0 | 0 | 1 | 0 | 2 |
| HFD + CDCArg | 0 | 0 | 1 | 0 | 0 | 1 |
| HFD + Arg | 2 | 0 | 1 | 0 | 0 | 3 |
| HFD + Arg | 1-2 | 0 | 0 | 0 | 0 | 1-2 |

*and megakarya
**oval cell proliferation
C = control,
HFD = high fat,
CA = cholic acid,
CDCArg = chenodeoxycholyl-arginine ethyl ester

TABLE 2

Modified Brunt Criteria of Staging and Grading NAFLD

| Steatosis | score (max = 4) |
|---|---|
| Macro and microvesicular steatosis | 0—None<br>1—Minimal (<10%)<br>2—Mild (10-33%)<br>3—Moderate (33-66%)<br>4—Severe (>66%) |
| Hepatitis (ballooning and inflammation) | score (max = 9) |
| Hepatocellular ballooning and disarray | 0—None<br>1—Occasional ballooning of zone 3 hepatocytes<br>2—Obvious ballooning of hepatocytes<br>3—Obvious ballooning and disarray of hepatocytes |
| Intraacinar (lobular) inflammation (leukocyte aggregations) | 0—None<br>1—1-2<br>2—up to 4<br>3—>4 |
| Portal tract inflammation | 0—None<br>1—Mild<br>2—Moderate<br>3—Severe |
| Staging (fibrosis) | score (max = 4) |
| Fibrosis score | 0—None<br>1—Zone 3 perisinusoidal/pericellular fibrosis, focally extensive present<br>2—Zone 3 perisinusoidal/pericellular fibrosis with focal or extensive periportal fibrosis<br>3—Zone 3 perisinusoidal/pericellular fibrosis, and portal fibrosis with focal extensive bridging fibrosis<br>4—Cirrhosis |

Example 3—Effects of CDCArg Following the Onset of Liver Steatosis in Mice Fed a High Fat Diet (HFD)

Experimental Design

Mice were randomly divided into two dietary groups:
1) Control diet: low-fat diet (LFD), 16% calories from fat (n=5);
2) High-fat diet (HFD): 60% calories from fat (mainly palm stearin) (n=16).

In order to determine the effects of CDCArg following the onset of liver steatosis, mice were first treated for 10 weeks with HFD to develop hepatic fat accumulation. Thereafter, the HFD-fed mice were divided to two equal groups (n=8 in each group): (a) continued the previous HFD treatment, and (b) HFD+CDCArg 0.5% w/w. In this part of the experiment mice were pair-fed (15.5 kCal/day per mice). The LFD control group consumed on average the same amount of calories per day per mice. The duration of treatment with CDCArg was four (4) weeks. Food consumption and gain of weight were evaluated.

Results

Figure 10A:
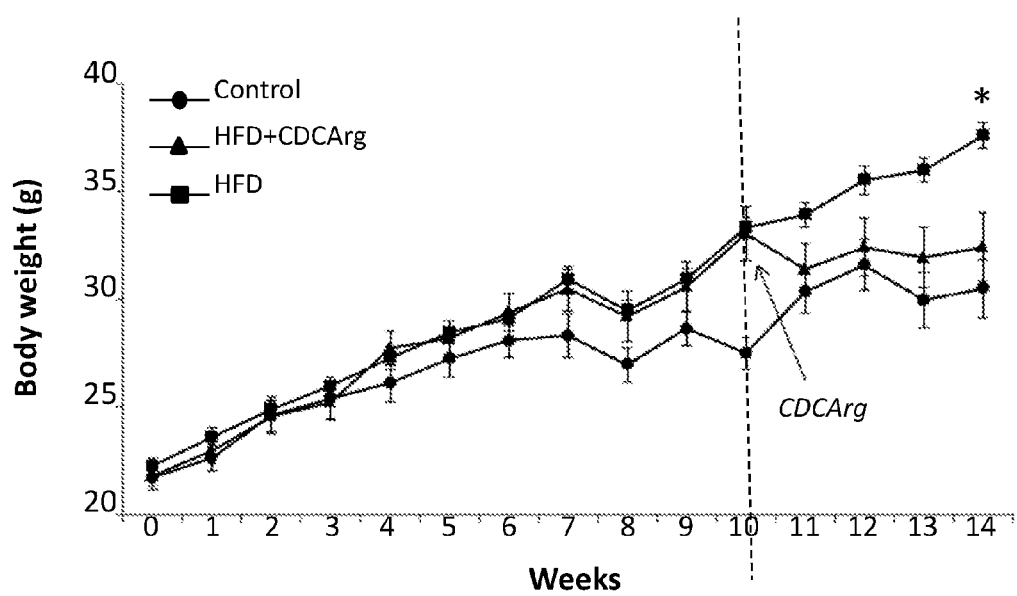
FIG. 10. Effects of CDCArg following the onset of liver steatosis in mice fed a high fat diet (HFD). Mice were allocated to two groups, one fed with LFD for 14 weeks, and the other fed with HFD for 10 weeks and then divided randomly into two equal groups that were pair-fed with HFD and HFD+CDCArg. (A) Mice weight as measured during the experiment at the beginning of each week (P<0.05, compared to HFD, ttest). The dashed vertical line indicates the beginning of CDCArg treatment (in one group); (B) Weight of adipose testicular tissue; (C) Fat percent in feces collected at week 10 before treatment with CDCArg (P<0.05, ttest); (D) Feces fat percent (week 13). Means with * are statistically higher than HFD group, p<0.05. n=6, ttest, (E) Average plasma albumin levels in treated mice (p<0.05. ttest).
Figure 10E:
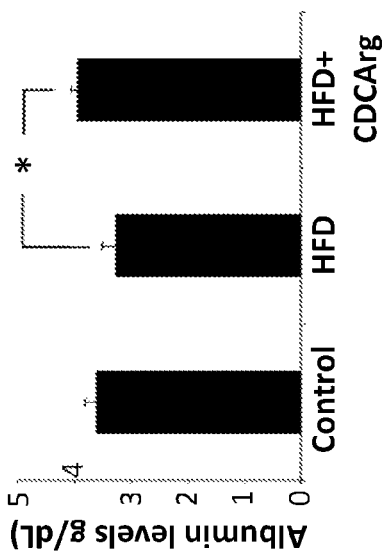
Figure 10D:
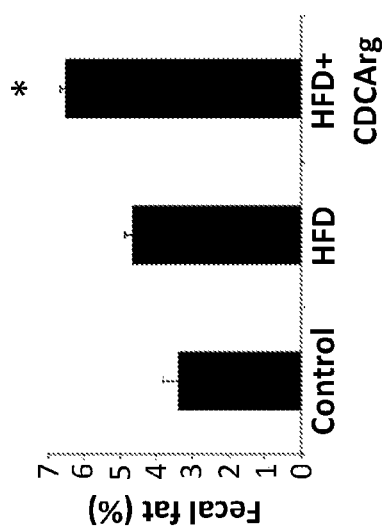
Figure 10B:
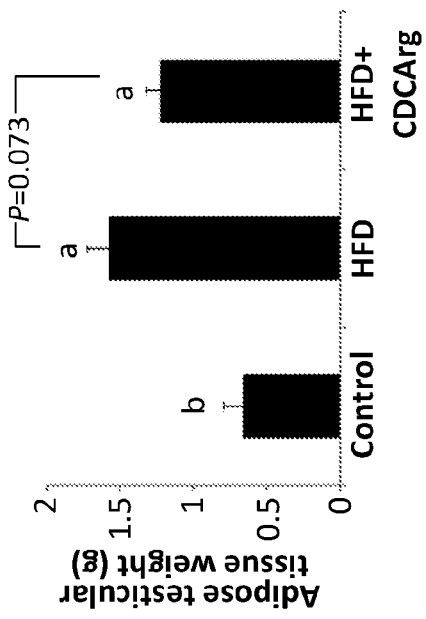
Figure 10C:
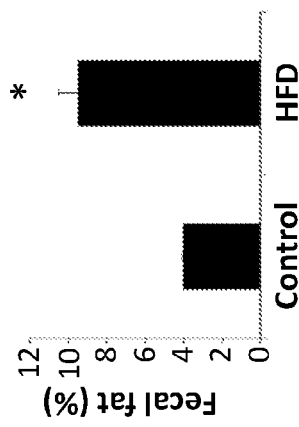
Figure 11A:
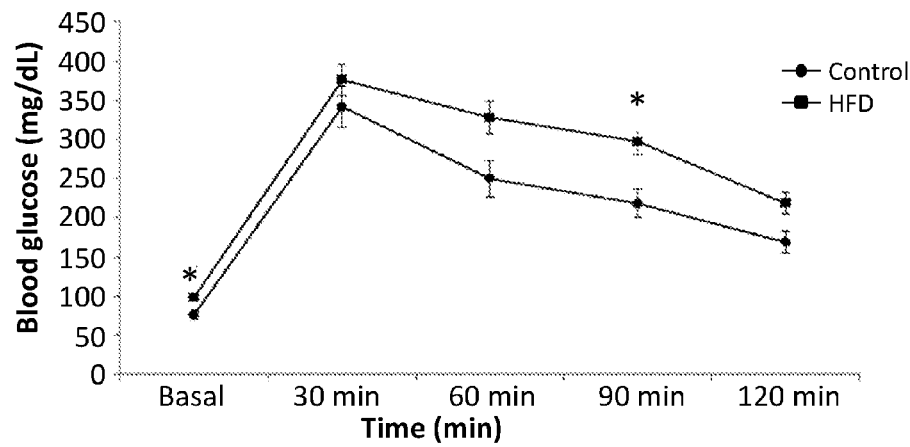
FIG. 11. Effect of CDCArg on insulin resistance as evaluated by intra-peritoneal glucose tolerance test (IPGTT). (A) IPGTT performed at weeks eight and (B) fourteen (before and after the beginning of treatment). Values are expressed as mean±SEM (n=8-9 animals per group). Means with * are statistically higher than Control group, p<0.05 (t.test (a) one way ANOVA, Post Hoc dunnett test (b)).
Figure 11B:
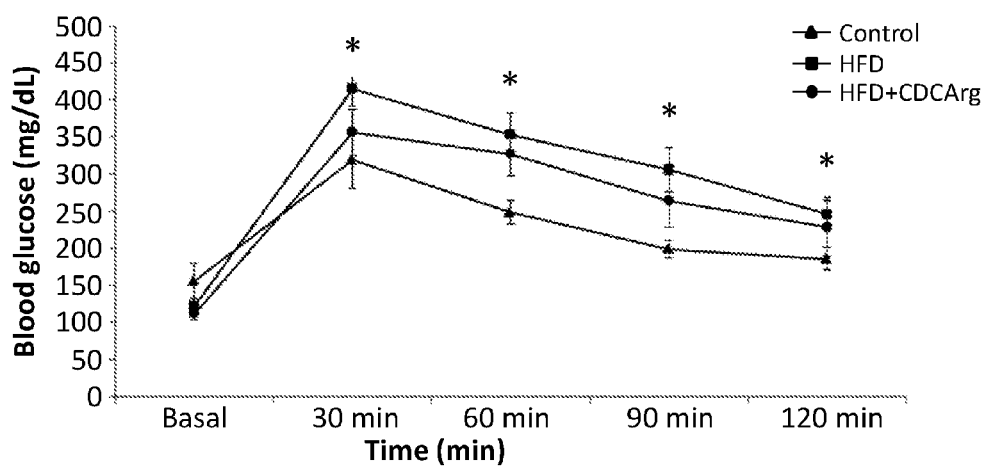

Weight and Metabolism:

As expected, consumption of HFD for 10 weeks led to an increase in total body weight. However, while body weight further increased in mice continuing to consume HFD for four additional weeks, the supplementation of CDCArg to HFD prevented this weight gain (FIG. 10a). Adipose tissue weight was also substantially lower in the HFD+CDCArg group compared to the HFD group (FIG. 10b). To assess the impact of CDCArg on intestinal absorption, fecal lipid contents were measured before and after CDCArg consumption. Total lipids were extracted from feces using Folch's method (Folch et al., 1957, *J Biol Chem,* 226:497-509) after collecting feces during weeks 9-10 and 12-13. As shown in FIGS. 10c and 10d, fat contents in feces were significantly higher in CDCArg treated mice (weeks 12-13). Thus, without being bound by any particular theory or mechanism of action, it seems that CDCArg, at least in part, inhibits intestinal fat absorption. Conversely, as indicated by plasma albumin levels, which was significantly higher in the HFD+CDCArg group than in the HFD group, it seems that protein absorption was not compromised by the supplementation of CDCArg (FIG. 10e). The effect of CDCArg on insulin resistance was evaluated using intraperitoneal glucose tolerance test (IPGTT). Glucose tolerance was assessed in the mice during the eighth and fourteenth weeks of the study (before and after the beginning of treatment with CDCArg). IPGTT was performed in 12 hours-fasted mice by injecting glucose (2 g/kg in 20% solution) intraperitoneally. Blood samples were obtained by cutting the tail tip and glucose concentration was measured after 0, 30, 60, 90, and 120 minutes. CDCArg improved metabolic parameters by lowering the peak glucose values in the IPGTT, and decreasing the area under the curve of the glycemic response (FIG. 11).

Figures 12A, 12B, 12C, 12D, 12E:
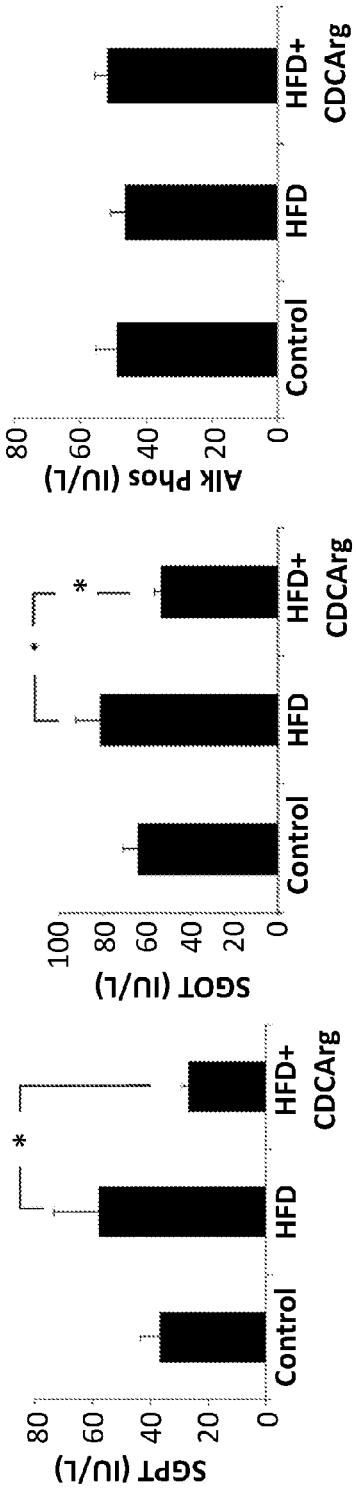
FIG. 12. Effect of CDCArg on plasma hepatic enzyme levels, liver weight and liver histology. (A-C) Average plasma SGPT, SGOT and Alkaline Phosphatase levels; (D) Liver weight; (E) Representative liver histologic sections stained with H&E (Magnification 200×).

Liver Protection Against HFD:

SGPT and SGOT levels were significantly lower in the HFD+CDCArg group compared with the HFD group (FIGS. 12a,b), while alkaline phosphatase levels in plasma were not significantly altered (FIG. 12c). Consistently, liver weight was also significantly lower in HFD+CDCArg group. Interestingly, liver weight in the HFD+CDCArg group was even lesser than in control (LFD) group (FIG. 12d). In agreement with the above results, histological evaluation revealed lesser liver micro and macro steatosis in the HFD+CDCArg group than in the HFD group (FIG. 12e). Lobular inflammation was also observed in the control group but not in the HFD+CDCArg group.

Effect on Energy Expenditure Genes and Lipogenesis Genes in the Liver:

Gene expression analysis showed that CDCArg activated genes that are related to energy expenditure, namely, PGC1α (peroxisome proliferator-activated receptor gamma coactivator 1-alpha) and PPARα, (peroxisome proliferator-activated receptor alpha), which may accelerate mitochondrial oxidation of fat. Additionally, CDCArg was found to suppress the protein expression of a key gene that regulates denovo lipogenesis, SREBP1c (sterol regulatory element-binding protein 1c) (FIG. 13). No statistical difference in AMPK (5' adenosine monophosphate-activated protein kinase) activation was observed in any of the treatments. However, the ratio of phosphorylated AMPK (pAMPK) to AMPK was tending to be higher in the HFD+CDCArg treated group.

Gene expression analyses of PPARα and PGC1α were performed by quantifying mRNA levels by reverse-transcription and real time PCR. GAPDH (glyceraldehyde 3-phosphate dehydrogenase) was used as housekeeping normalizing gene. The following primers were used:

```
PPAR-alpha
                                   (SEQ ID NO: 1)
f-5'-GTCACACAATGCAATTCGCTTT-3'

PPAR-alpha
                                   (SEQ ID NO: 2)
r-5'-TTTGCTTTTTCAGATCTTGGCA-3'

PGC-1 alpha
                                   (SEQ ID NO: 3)
f-5'-AAACCC TGCCATTGTTAAG-3'

PGC-1 alpha
                                   (SEQ ID NO: 4)
r-5'-TGACAAATGCTCTTCGCTTT-3'

GAPDH
                                   (SEQ ID NO: 5)
f-5'-GCATCTTGGGCTACACTGAG-3'

GAPDH
                                   (SEQ ID NO: 6)
f-5'-AGAGTGGGAGTTGCTGTTGA-3'
```

SREBP1c was analyzed by Western blot analysis using beta-actin as control. Abs: Anti SREBP-1 Santa Cruse (Sc-367); Secondary goat Anti-Rabbit IgG, Jackson ImmunoResearch, Mouse Anti-Actin (612656) BD Transduction Laboratories. Secondary goat Anti-mouse IgG, Jackson ImmunoResearch.

The levels of AMPK and pAMPK were analyzed using Western blot analysis.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A compound selected from the group consisting of:

(i) a compound having the structure of Formula (Ia) or a pharmaceutically acceptable salt thereof:

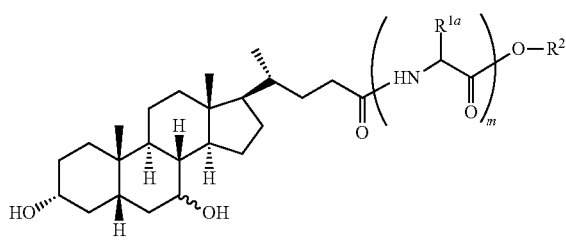

(Ia)

wherein
m=1;
$R^{1a}$ represents the side chain of arginine; and
$R^2$ represents $C_1$-$C_4$ alkyl;

(ii) a compound having the structure of Formula (Ib) or a pharmaceutically acceptable salt thereof:

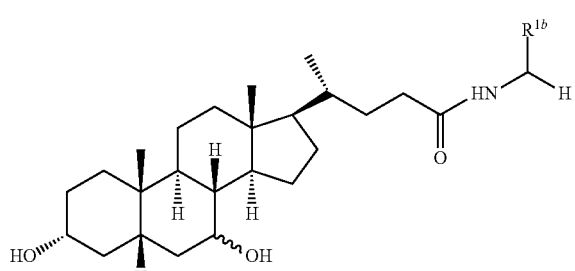

(Ib)

wherein
$R^{1b}$ is the side chain of agmatine;

(iii) a compound having the structure of Formula (Ic) or a pharmaceutically acceptable salt thereof:

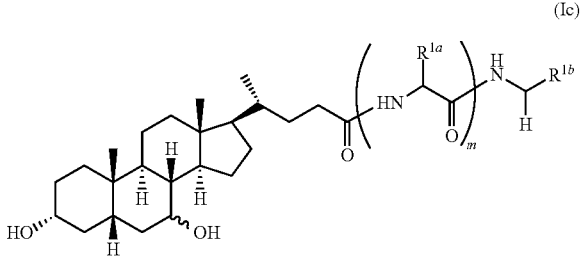

(Ic)

wherein $R^{1a}$ and $R^{1b}$ are as defined above; and (iv) a compound having the structure of Formula (II) or a pharmaceutically acceptable salt thereof:

(II)

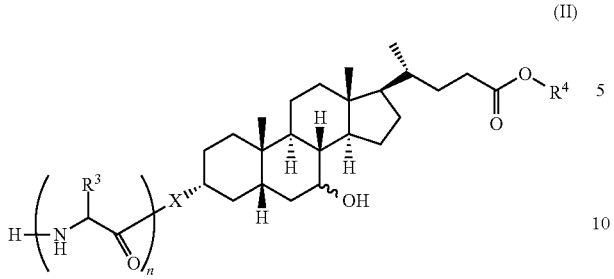

wherein

X is O or NH;

n is an integer of 1 to 2;

$R^3$ independently at each occurrence (out of the n occurrences) represents the side chain of arginine; and $R^4$ represents H, a $C_1$-$C_4$ alkyl, or M wherein M is a counter-ion.

2. The compound according to claim 1, wherein either $R^2$ or $R^4$ are ethyl.

3. The compound according to claim 1, which is a derivative of chenodeoxycholic acid or urosodeoxycholic acid.

4. The compound according to claim 1, which is selected from the group consisting of:

compound (1)

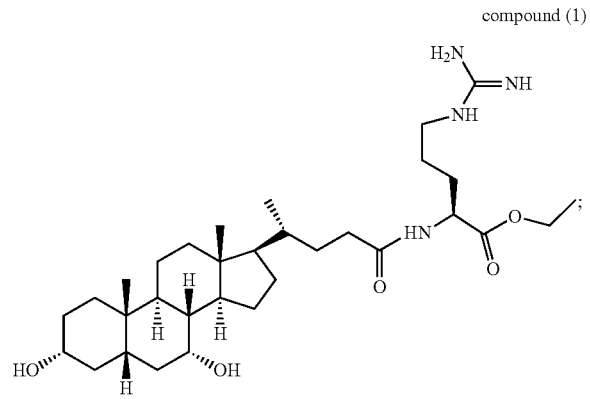

compound (2)

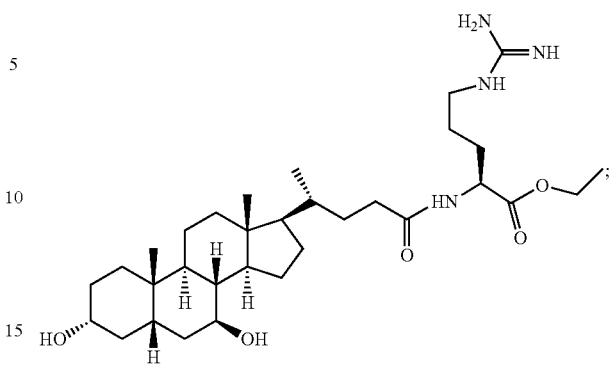

and pharmaceutically acceptable salts thereof.

5. The compound according to claim 4, having the structure of compound (1):

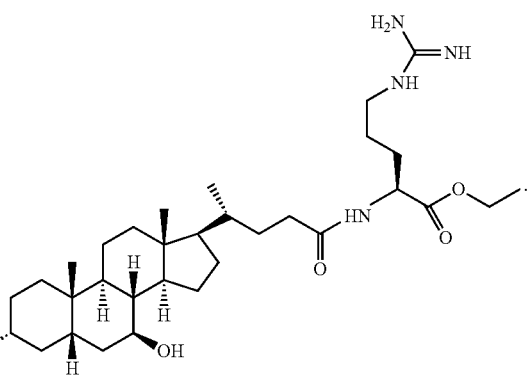

6. A method for treating a disease or disorder associated with metabolic syndrome in a subject in need thereof, the method comprising the step of administering to the subject a pharmaceutical composition comprising as an active ingredient the compound of claim 1.

7. The method according to claim 6, wherein the disease or disorder associated with the metabolic syndrome is selected from the group consisting of obesity, excessive weight, dyslipidemia, hyperglycemia, hyperleptinemia, hyperinsulinemia, pre-diabetes, type-2 diabetes, hypertension and a fatty liver disorder.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gtcacacaat gcaattcgct tt                                        22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2 tttgctttttt cagatcttgg ca                                       22

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
```

```
aaaccctgcc attgttaag                                           19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgacaaatgc tcttcgcttt                                          20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcatcttggg ctacactgag                                          20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
agagtgggag ttgctgttga                                          20
```